United States Patent
Liang et al.

(10) Patent No.: US 8,160,834 B2
(45) Date of Patent: Apr. 17, 2012

(54) METHODS AND SYSTEMS FOR OBSERVING SENSOR PARAMETERS

(75) Inventors: Bradley Chi Liang, Bloomfield Hills, MI (US); Larry E. Tyler, Mesa, AZ (US); Mohsen Askarinya, Chandler, AZ (US); Charles R. Gordon, Phoenix, AZ (US); Randal C. Schulhauser, Phoenix, AZ (US); Kenneth W. Cooper, Valencia, CA (US); Kris R. Holtzclaw, Santa Clarita, CA (US); Brian T. Kannard, Los Angeles, CA (US); Rajiv Shah, Rancho Palos Verdes, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

(21) Appl. No.: 13/151,601

(22) Filed: Jun. 2, 2011

(65) Prior Publication Data

US 2011/0230741 A1    Sep. 22, 2011

Related U.S. Application Data

(62) Division of application No. 12/345,354, filed on Dec. 29, 2008.

(51) Int. Cl.
*G01C 19/00* (2006.01)
*G01C 25/00* (2006.01)
*G01R 25/00* (2006.01)

(52) U.S. Cl. ............................ 702/104; 702/116; 702/65

(58) Field of Classification Search .................... 702/65, 702/104, 116, 64, 182; 324/600, 609
See application file for complete search history.

(56) References Cited

U.S. PATENT DOCUMENTS

| | | | |
|---|---|---|---|
| 6,275,717 B1 | 8/2001 | Gross et al. | |
| 7,727,148 B2 * | 6/2010 | Talbot et al. | 600/365 |
| 7,774,038 B2 * | 8/2010 | Wang et al. | 600/345 |
| 2006/0020186 A1 | 1/2006 | Brister et al. | |
| 2007/0169533 A1 * | 7/2007 | Shah et al. | 73/1.01 |
| 2007/0173711 A1 | 7/2007 | Shah et al. | |
| 2007/0173712 A1 * | 7/2007 | Shah et al. | 600/347 |
| 2007/0299617 A1 | 12/2007 | Willis | |
| 2008/0000779 A1 * | 1/2008 | Wang et al. | 205/775 |
| 2008/0161664 A1 | 7/2008 | Mastrototaro et al. | |
| 2010/0025238 A1 * | 2/2010 | Gottlieb et al. | 204/401 |
| 2010/0169035 A1 * | 7/2010 | Liang et al. | 702/65 |

FOREIGN PATENT DOCUMENTS

| WO | 96/14026 | 5/1996 |
|---|---|---|
| WO | 2006/008505 | 1/2006 |

OTHER PUBLICATIONS

"RF Café—Capacitors & Capacitance Calculations Formulas Equations," Internet Archive Wayback Machine, Oct. 18, 2007, http://replay.web.archive.org/ 2007/20071018033322/http://www.rfcafe.com/references/electrical/capacitance.htm. International Search Report and Written Opinion, International application No. PCT/US2009/069600, International filing date Dec. 28, 2009, mailed Oct. 22, 2010.

\* cited by examiner

*Primary Examiner* — Michael Nghiem
*Assistant Examiner* — Manuel Rivera Vargas
(74) *Attorney, Agent, or Firm* — Gates & Cooper LLP

(57) ABSTRACT

The invention disclosed herein provides methods and materials for observing the state of a sensor, for example those used by diabetic patients to monitor blood glucose levels. Typically a voltage such as a voltage pulse is applied to the sensor in order to solicit a current response from which for example, factors such as impedance values can be derived. Such values can then be used as indicators of a sensor's state, for example the state of sensor hydration, sensor noise, sensor offset, sensor drift or the like.

9 Claims, 26 Drawing Sheets

METHODS AND SYSTEMS FOR OBSERVING SENSOR PARAMETERS

CROSS REFERENCE TO RELATED APPLICATIONS

This application is a divisional application which claims priority from U.S. patent application Ser. No. 12/345,354, filed Dec. 29, 2008, the contents of which are incorporated herein by reference. This application is related to U.S. patent application Ser. No. 11/322,977; U.S. patent application Ser. No. 11/323,242; U.S. patent application Ser. No. 11/842,825; U.S. patent application Ser. No. 11/980,149, now U.S. Pat. No. 7,727,148; U.S. patent application Ser. No. 11/323,216, now U.S. Pat. No. 7,774,038; U.S. patent application Ser. No. 11/633,254, and U.S. patent application Ser. No. 12/184,046, the contents of which are herein incorporated by reference.

FIELD OF THE INVENTION

Embodiments of this invention provide methods and systems for determining the state of sensors, for example the sufficiency of hydration of a glucose sensor during its initial use.

DESCRIPTION OF RELATED ART

In many medical conditions medical personnel gain valuable information by monitoring the readings of physiological conditions within a patient's body. For example, many patients suffering from diabetes typically monitor their blood glucose levels on a continuing basis. Typically, diabetics can measure their blood glucose (BG) using a BG measurement device, such as a test strip meter, a continuous glucose measurement system, or a hospital hemacue. BG measurement devices use various methods to measure the BG level of a patient, such as a sample of the patient's blood, a sensor in contact with a bodily fluid, an optical sensor, an enzymatic sensor, or a fluorescent sensor.

Current continuous glucose measurement systems include subcutaneous (or short-term) sensors and implantable (or long-term) sensors. For each of the short-term sensors and the long-term sensors, a patient has to wait a certain amount of time in order for the continuous glucose sensor to stabilize and to provide accurate readings. In many continuous glucose sensors, the subject must wait three hours for the continuous glucose sensor to stabilize before any glucose measurements are utilized. This is an inconvenience for the patient and in some cases may cause the patient not to utilize a continuous glucose measurement system.

Further, when a sensor such as a glucose sensor is implanted in a patient, started up and then used to monitor glucose, the glucose sensor may not operate in a stable state. For example, the electrical readings from the sensor, which optimally are directly correlated to the glucose level of the patient, can nonetheless vary and are subject to factors which confound sensor readings, for example erroneous reading that can result from phenomena such as sensor dehydration, sensor noise, sensor drift and the like.

BRIEF SUMMARY OF THE INVENTION

Embodiments of the invention disclosed herein include methods and materials for observing and characterizing the state of a sensor for example a glucose sensor used by a diabetic patient. Illustrative embodiments of the invention include a sensor system having a plurality of electrodes and a sensor electronics device which includes a connection device, a power source, an electrical circuit and a microcontroller. In typical embodiments of the invention, the electrical circuit is used in methods that characterize the state of sensor elements, for example whether one or more electrodes in the sensor is hydrated and/or operating within a range of predetermined functional parameters.

The invention disclosed herein has a number of embodiments. A typical embodiments of the invention is a method of observing a state of a sensor having a plurality of electrodes, the method comprising applying voltage to the sensor, observing a peak instantaneous electrical current of the sensor, and observing a total current of the sensor over a period of time for a predetermined frequency so that the state of the sensor is observed. Such methods of the invention can be used to observe a number of measurable and/or quantifiable sensor characteristics. For example, observations of the peak instantaneous electrical current and/or the total current in the sensor over a period of time for a predetermined frequency can be used to estimate sensor impedance magnitude and/or sensor capacitance. Typically such observations on the states or characteristics of a sensor are used to obtain information associated with sensor operation in vivo, for example the presence or levels of sensor hydration, sensor noise, sensor offset, sensor drift or the like.

Embodiments of the invention include a variety of ways in which observations on the state or characteristics of a sensor can be obtained. For example, certain embodiments of the invention are designed to estimate a state of sensor capacitance, wherein an estimate of sensor capacitance comprises a voltage step analysis using a mathematical formula:

$$C \approx \frac{\sum_{n=1}^{n \leq dt} dI * t_{samp}}{dV}$$

In this formula, C comprises capacitance, V comprises voltage, dV comprises a controlled voltage step, dt comprises a length of time for analysis, $t_{samp}$ comprises a length of time between samples, and dI comprises a change in current.

Embodiments of the invention employ a variety of different methodological steps to observe sensor characteristics. For example, certain embodiments of the invention comprise applying a voltage pulse to the sensor. In one illustrative embodiment, the method comprises observing the maximum current value (counts/second) during the initial 2 seconds in response to a voltage pulse applied to the sensor, and then comparing the maximum current value to a predetermined test value. In other embodiments, the methods comprises methodological steps such as applying a plurality of voltages to the sensor and/or observing current in the sensor over multiple periods of time and/or observing current in the sensor over multiple frequencies. Some embodiments of the invention are designed for use in manufacturing processes, for example to examine the uniformity of a lot of sensors manufactured according to a specific process (e.g. by performing the methods on a plurality of sensors; and then comparing the information so obtained on the state of the plurality of sensors).

Embodiments of the invention can be adapted for use with a wide variety of electrochemical sensors such as glucose sensors that comprise glucose oxidase. In one such embodiment of the invention, the glucose sensor comprises a base layer, at least three working electrodes disposed on the base layer, a glucose oxidase layer disposed upon the working electrodes, an analyte modulating layer disposed on the glucose oxidase layer, wherein the analyte modulating layer comprises a hydrogel composition, and an adhesion promoting layer disposed between the glucose oxidase layer and the analyte modulating layer. Optionally embodiments of the sensor comprise a plurality of working electrodes and/or counter electrodes and/or reference electrodes (e.g. 3 working electrodes, a reference electrode and a counter electrode), in order to, for example, provide redundant sensing capabilities. Optionally, the plurality of working, counter and reference electrodes are configured together as a unit and positionally distributed on the conductive layer in a repeating pattern of units.

Embodiment of the invention include sensor systems such as those comprising an implantable sensor having a plurality of electrodes and a sensor electronics device that is operably connected to the sensor. Typically, the sensor electronics device includes a connection detection device to determine if the sensor electronics device is connected to the sensor and to transmit a connection signal, a power source to supply a regulated voltage, and a microprocessor. Such systems typically include a computer-readable program code having instructions, which when executed cause the microprocessor to apply a voltage to the sensor and then record data on a peak instantaneous electrical current of the sensor in response to the applied voltage as well as record data on a total current of the sensor over a period of time for a predetermined frequency in response to the applied voltage. Typically the system further comprises a monitor for displaying the data recorded by the microprocessor, wherein the data displayed on the monitor provides information on sensor hydration, sensor noise, sensor offset, sensor drift or the like. Optionally in such systems, the implantable sensor is a glucose sensor comprising a base layer, at least three working electrodes disposed on the base layer, a glucose oxidase layer disposed upon the working electrodes, an analyte modulating layer disposed on the glucose oxidase layer; and an adhesion promoting layer disposed between the glucose oxidase layer and the analyte modulating layer. Typically the sensor is implantable in tissue selected from the group consisting of subcutaneous, dermal, sub-dermal, intra-peritoneal, and peritoneal tissue.

Yet another embodiment of the invention is a program code storage device comprising a computer-readable medium, a computer-readable program code, stored on the computer-readable medium, the computer-readable program code having instructions, which when executed cause a controller to initiate a series of voltage pulses to be applied to a sensor comprising a plurality of electrodes; and receive a signal from a detection circuit, the signal indicating a peak instantaneous electrical current of the sensor in response to the applied voltage pulses; and a total current of the sensor over a period of time for a predetermined frequency in response to the applied voltage pulses. Optionally the program code storage device includes instructions, which when executed causes the controller to determine the maximum current value (counts/second) during the initial 2 seconds in response to a voltage pulse applied to the sensor, and then compare the maximum current value so determined to a predetermined range of values. In certain embodiments of the invention, the program code storage device includes instructions, which when executed causes the controller to then enable the sensor to measure a physiological characteristic of a patient when the maximum current value is within the predetermined range of values.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

A detailed description of embodiments of the invention will be made with reference to the accompanying drawings, wherein like numerals designate corresponding parts in the figures.

DETAILED DESCRIPTION OF THE INVENTION

Figure 1:
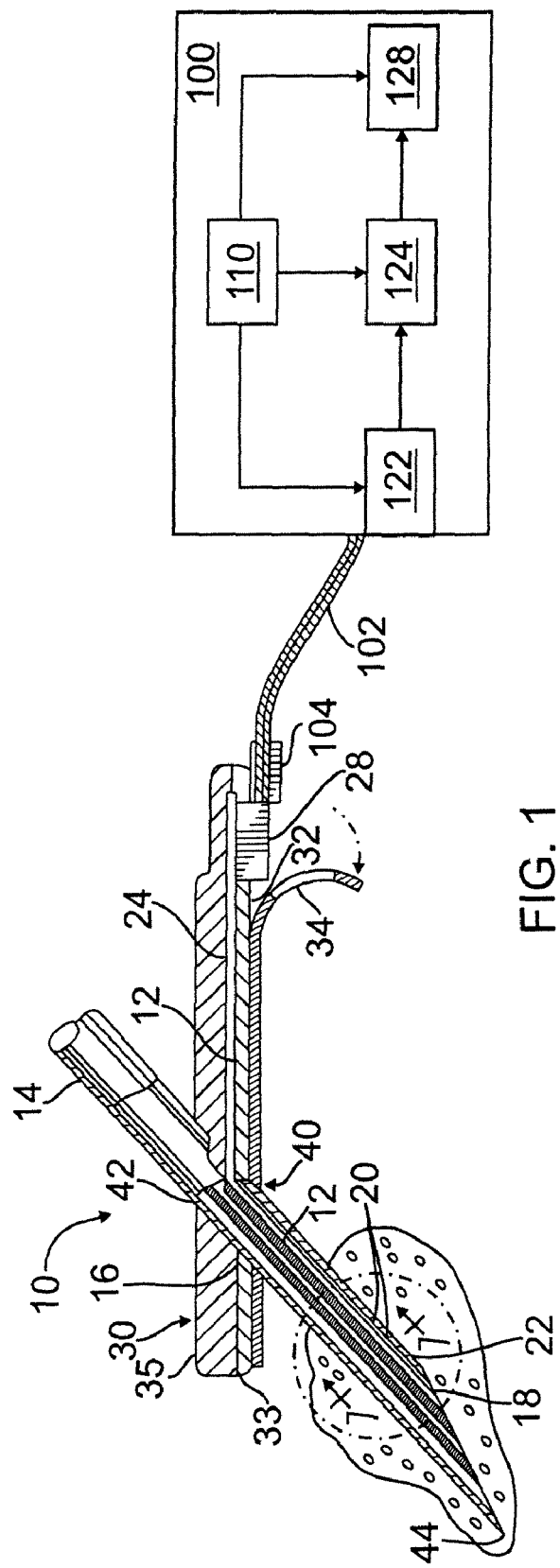
FIG. 1 is a perspective view of a subcutaneous sensor insertion set and block diagram of a sensor electronics device according to an embodiment of the invention.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. A number of terms are defined below.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

Before the present compositions and methods etc. are described, it is to be understood that this invention is not limited to the particular methodology, protocol and reagent described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a voltage", "a time", "frequency" includes a plurality of such and equivalents thereof known to those skilled in the art, and so forth. All numbers recited in the specification and associated claims that refer to values that can be numerically characterized with a value other than a whole number (e.g. the concentration of a compound in a solution) are understood to be modified by the term "about".

The term "analyte" as used herein is a broad term and is used in its ordinary sense, including, without limitation, to refer to a substance or chemical constituent in a fluid such as a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to, lactate. Salts, sugars, protein fats, vitamins and hormones naturally occurring in blood or interstitial fluids can constitute analytes in certain embodiments. The analyte can be naturally present in the biological fluid or endogenous; for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin. The metabolic products of drugs and pharmaceutical compositions are also contemplated analytes.

In the following description, reference is made to the accompanying drawings which form a part hereof and which illustrate several embodiments of the present inventions. It is understood that other embodiments may be utilized and structural and operational changes may be made without departing from the scope of the present inventions.

Determining the state of a sensor such as an electrochemical glucose sensor has traditionally been performed by using a standard timer function. However, there is an increasing need to limit the use of the sensor to a specified duration to avoid problems associated with off-label use. Such problems can be addressed using embodiments of the invention disclosed herein, for example by using a voltage pulse to solicit a current response, in which complex impedance values are derived. These then impedance values provide an indicator of the sensor's state (pre vs. post initialization). Embodiments of the invention can then limit the use of a commercial sensor to its regulatory agency approved labeling standard (e.g. 3 or 6 days). Embodiments of the invention analyze electrochemical properties of a sensor to determine its overall health (i.e. operability parameters). Applications for embodiments of the invention include for example: optimizing sensor startup and/or to prevent the use of old sensors; the prevention of a startup/initialization sequence for non-hydrated and/or incompletely hydrated sensors; to indicate when sensors begin to provide bad data (e.g. bad data that results from noise, drift and the like.); and to provide corrective measures to changes in the state of the sensor (e.g. adjusting for drift or changes in sensor offset).

Embodiments of the invention relate to Electrochemical Impedance Spectroscopy (EIS) and analogs thereof. Without being bound by a specific scientific theory, evidence indicates that a sensor operating for example in vivo undergoes changes in impedance. As impedance can be difficult to determine using conventional methods, an analogue test for the GST(R) can be useful in a variety of situations. Embodiments of the invention observe: (1) capacitance to estimate the imaginary component of complex impedance; and (2) current response because for example a different current with same voltage in a sensor provides evidence that some parameter of sensor function has changed. In one typical capacitance estimation, the sum of counts over sample time provides an indication of sensor charge capacity. The current analysis can then for example analyze changes in counts/sec given a specific voltage (e.g. 10 mV). In this context, these factors can be used to provide an analogue for impedance magnitude and are further helpful in determining noise level as well. In this way, embodiments of the invention combine current and capacitive analysis as a simple and elegant way to diagnose sensor health.

The present invention described below with reference to flowchart illustrations of methods, apparatus, and computer program products. It will be understood that each block of the flowchart illustrations, and combinations of blocks in the flowchart illustrations, can be implemented by computer program instructions (as can any menu screens described in the Figures). These computer program instructions may be loaded onto a computer or other programmable data processing apparatus (such as a controller, microcontroller, microprocessor or the like) in a sensor electronics device to produce a machine, such that the instructions which execute on the computer or other programmable data processing apparatus create instructions for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks, and/or menus presented herein.

FIG. 1 is a perspective view of a subcutaneous sensor insertion set and a block diagram of a sensor electronics device according to an embodiment of the invention. As illustrated in FIG. 1, a subcutaneous sensor set 10 is provided for subcutaneous placement of an active portion of a flexible sensor 12 (see FIG. 2), or the like, at a selected site in the body of a user. The subcutaneous or percutaneous portion of the sensor set 10 includes a hollow, slotted insertion needle 14, and a cannula 16. The needle 14 is used to facilitate quick and easy subcutaneous placement of the cannula 16 at the subcutaneous insertion site. Inside the cannula 16 is a sensing portion 18 of the sensor 12 to expose one or more sensor electrodes 20 to the user's bodily fluids through a window 22 formed in the cannula 16. In an embodiment of the invention, the one or more sensor electrodes 20 may include a counter electrode, a working electrode, and a reference electrode. Optionally embodiments of the sensor comprise a plurality of working electrodes and/or counter electrodes and/or reference electrodes (e.g. 3 working electrodes, a reference electrode and a counter electrode), in order to, for example, provide redundant sensing capabilities. Optionally, the plurality of working, counter and reference electrodes are configured together as a unit and positionally distributed on the conductive layer in a repeating pattern of units. After insertion of the sensor, the insertion needle 14 is withdrawn to leave the cannula 16 with the sensing portion 18 and the sensor electrodes 20 in place at the selected insertion site.

In particular embodiments, the subcutaneous sensor set 10 facilitates accurate placement of a flexible thin film electrochemical sensor 12 of the type used for monitoring specific blood parameters (i.e. measurable and/or quantifiable characteristics) representative of a user's condition. The sensor 12 monitors glucose levels in the body, and may be used in conjunction with automated or semi-automated medication infusion pumps of the external or implantable type as described in U.S. Pat. Nos. 4,562,751; 4,678,408; 4,685,903 or 4,573,994, to control delivery of insulin to a diabetic patient.

Particular embodiments of the flexible electrochemical sensor 12 are constructed in accordance with thin film mask techniques to include elongated thin film conductors embedded or encased between layers of a selected insulative material such as polyimide film or sheet, and membranes. The sensor electrodes 20 at a tip end of the sensing portion 18 are exposed through one of the insulative layers for direct contact with patient blood or other body fluids, when the sensing portion 18 (or active portion) of the sensor 12 is subcutaneously placed at an insertion site. The sensing portion 18 is joined to a connection portion 24 that terminates in conductive contact pads, or the like, which are also exposed through one of the insulative layers. In alternative embodiments, other types of implantable sensors, such as chemical based, optical based, or the like, may be used.

As is known in the art, the connection portion 24 and the contact pads are generally adapted for a direct wired electrical connection to a suitable monitor or sensor electronics device 100 for monitoring a user's condition in response to signals derived from the sensor electrodes 20. Further description of flexible thin film sensors of this general type are be found in U.S. Pat. No. 5,391,250, entitled METHOD OF FABRICATING THIN FILM SENSORS, which is herein incorporated by reference. The connection portion 24 may be conveniently connected electrically to the monitor or sensor electronics device 100 or by a connector block 28 (or the like) as shown and described in U.S. Pat. No. 5,482,473, entitled FLEX CIRCUIT CONNECTOR, which is also herein incorporated by reference. Thus, in accordance with embodiments of the present invention, subcutaneous sensor sets 10 may be configured or formed to work with either a wired or a wireless characteristic monitor system.

The sensor electrodes 10 may be used in a variety of sensing applications and may be configured in a variety of ways. For example, the sensor electrodes 10 may be used in physiological parameter sensing applications in which some type of biomolecule is used as a catalytic agent. For example, the sensor electrodes 10 may be used in a glucose and oxygen sensor having a glucose oxidase enzyme catalyzing a reaction with the sensor electrodes 20. The sensor electrodes 10, along with a biomolecule or some other catalytic agent, may be placed in a human body in a vascular or non-vascular environment. For example, the sensor electrodes 20 and biomolecule may be placed in a vein and be subjected to a blood stream, or may be placed in a subcutaneous or peritoneal region of the human body.

The monitor 100 may also be referred to as a sensor electronics device 100. The monitor 100 may include a power source 110, a sensor interface 122, processing electronics 124, and data formatting electronics 128. The monitor 100 may be coupled to the sensor set 10 by a cable 102 through a connector that is electrically coupled to the connector block 28 of the connection portion 24. In an alternative embodiment, the cable may be omitted. In this embodiment of the invention, the monitor 100 may include an appropriate connector for direct connection to the connection portion 104 of the sensor set 10. The sensor set 10 may be modified to have the connector portion 104 positioned at a different location, e.g., on top of the sensor set to facilitate placement of the monitor 100 over the sensor set.

In embodiments of the invention, the sensor interface 122, the processing electronics 124, and the data formatting electronics 128 are formed as separate semiconductor chips, however alternative embodiments may combine the various semiconductor chips into a single or multiple customized semiconductor chips. The sensor interface 122 connects with the cable 102 that is connected with the sensor set 10.

The power source 110 may be a battery. The battery can include three series silver oxide 357 battery cells. In alternative embodiments, different battery chemistries may be utilized, such as lithium based chemistries, alkaline batteries, nickel metalhydride, or the like, and different number of batteries may used. The monitor 100 provides power, through the power source 110, provides power, through the cable 102 and cable connector 104 to the sensor set. In an embodiment of the invention, the power is a voltage provided to the sensor set 10. In an embodiment of the invention, the power is a current provided to the sensor set 10. In an embodiment of the invention, the power is a voltage provided at a specific voltage to the sensor set 10.

Figure 2A:
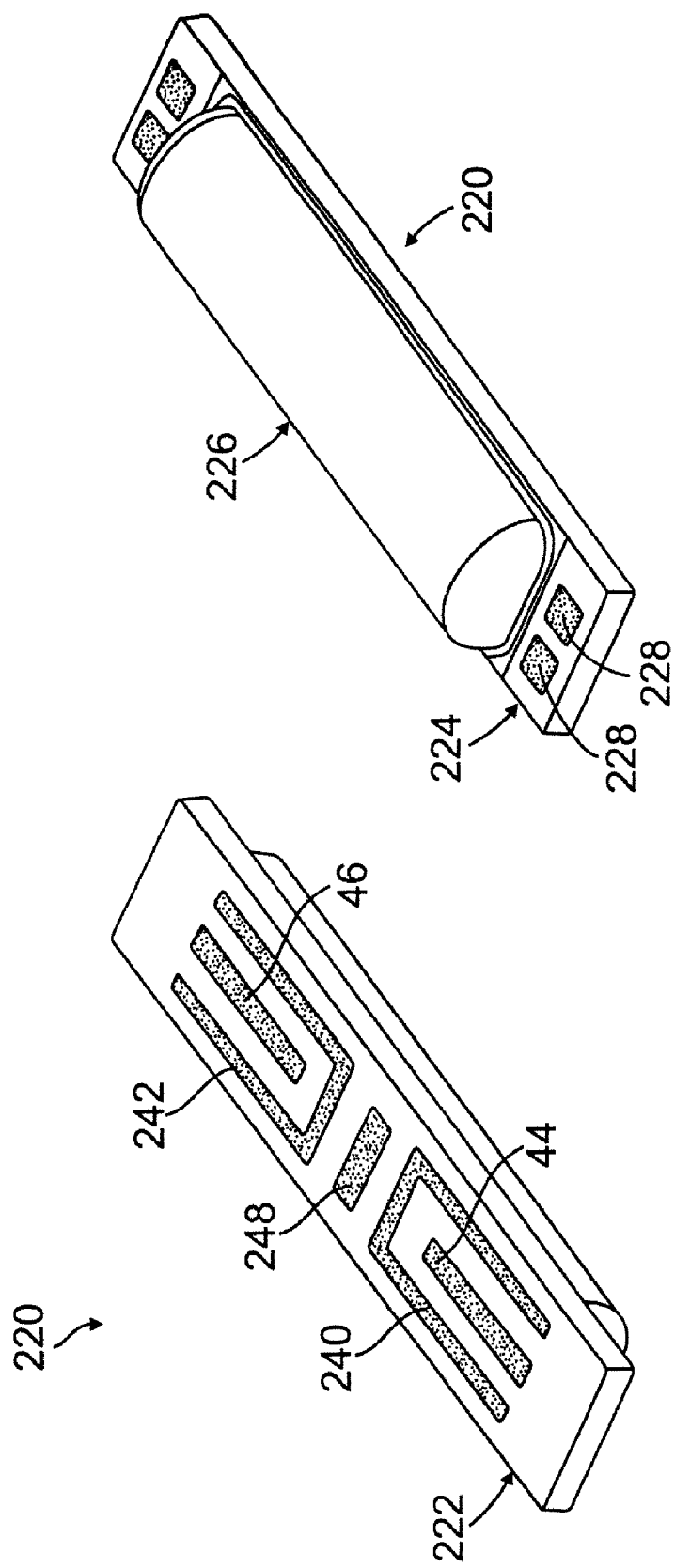
FIG. 2(a) illustrates a substrate having two sides, a first side which contains an electrode configuration and a second side which contains electronic circuitry.
Figure 2B:
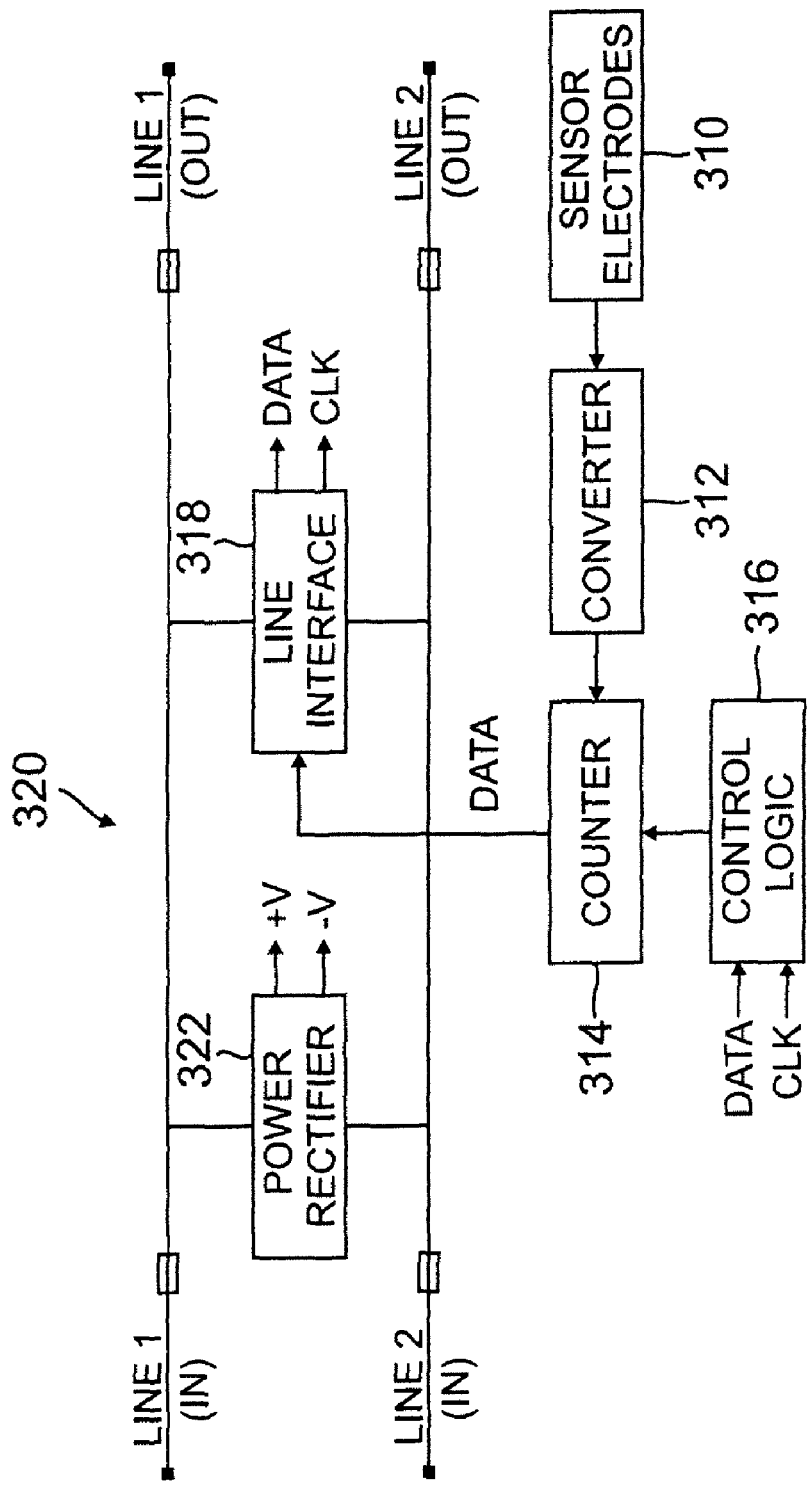
FIG. 2(b) illustrates a general block diagram of an electronic circuit for sensing an output of a sensor.

FIGS. 2(a) and 2(b) illustrates an implantable sensor and electronics for driving the implantable sensor according to an embodiment of the present invention. FIG. 2(a) shows a substrate 220 having two sides, a first side 222 of which contains an electrode configuration and a second side 224 of which contains electronic circuitry. As may be seen in FIG. 2(a), a first side 222 of the substrate comprises two counter electrode-working electrode pairs 240, 242, 244, 246 on opposite sides of a reference electrode 248. A second side 224 of the substrate comprises electronic circuitry. As shown, the electronic circuitry may be enclosed in a hermetically sealed casing 226, providing a protective housing for the electronic circuitry. This allows the sensor substrate 220 to be inserted into a vascular environment or other environment, which may subject the electronic circuitry to fluids. By sealing the electronic circuitry in a hermetically sealed casing 226, the electronic circuitry may operate without risk of short circuiting by the surrounding fluids. Also shown in FIG. 2(a) are pads 228 to which the input and output lines of the electronic circuitry may be connected. The electronic circuitry itself may be fabricated in a variety of ways. According to an embodiment of the present invention, the electronic circuitry may be fabricated as an integrated circuit using techniques common in the industry.

FIG. 2(b) illustrates a general block diagram of an electronic circuit for sensing an output of a sensor according to an embodiment of the present invention. At least one pair of sensor electrodes 310 may interface to a data converter 312, the output of which may interface to a counter 314. The counter 314 may be controlled by control logic 316. The output of the counter 314 may connect to a line interface 318. The line interface 318 may be connected to input and output lines 320 and may also connect to the control logic 316. The input and output lines 320 may also be connected to a power rectifier 322.

The sensor electrodes 310 may be used in a variety of sensing applications and may be configured in a variety of ways. For example, the sensor electrodes 310 may be used in physiological parameter sensing applications in which some type of biomolecule is used as a catalytic agent. For example, the sensor electrodes 310 may be used in a glucose and oxygen sensor having a glucose oxidase enzyme catalyzing a reaction with the sensor electrodes 310. The sensor electrodes 310, along with a biomolecule or some other catalytic agent, may be placed in a human body in a vascular or non-vascular environment. For example, the sensor electrodes 310 and biomolecule may be placed in a vein and be subjected to a blood stream.

Figure 3:
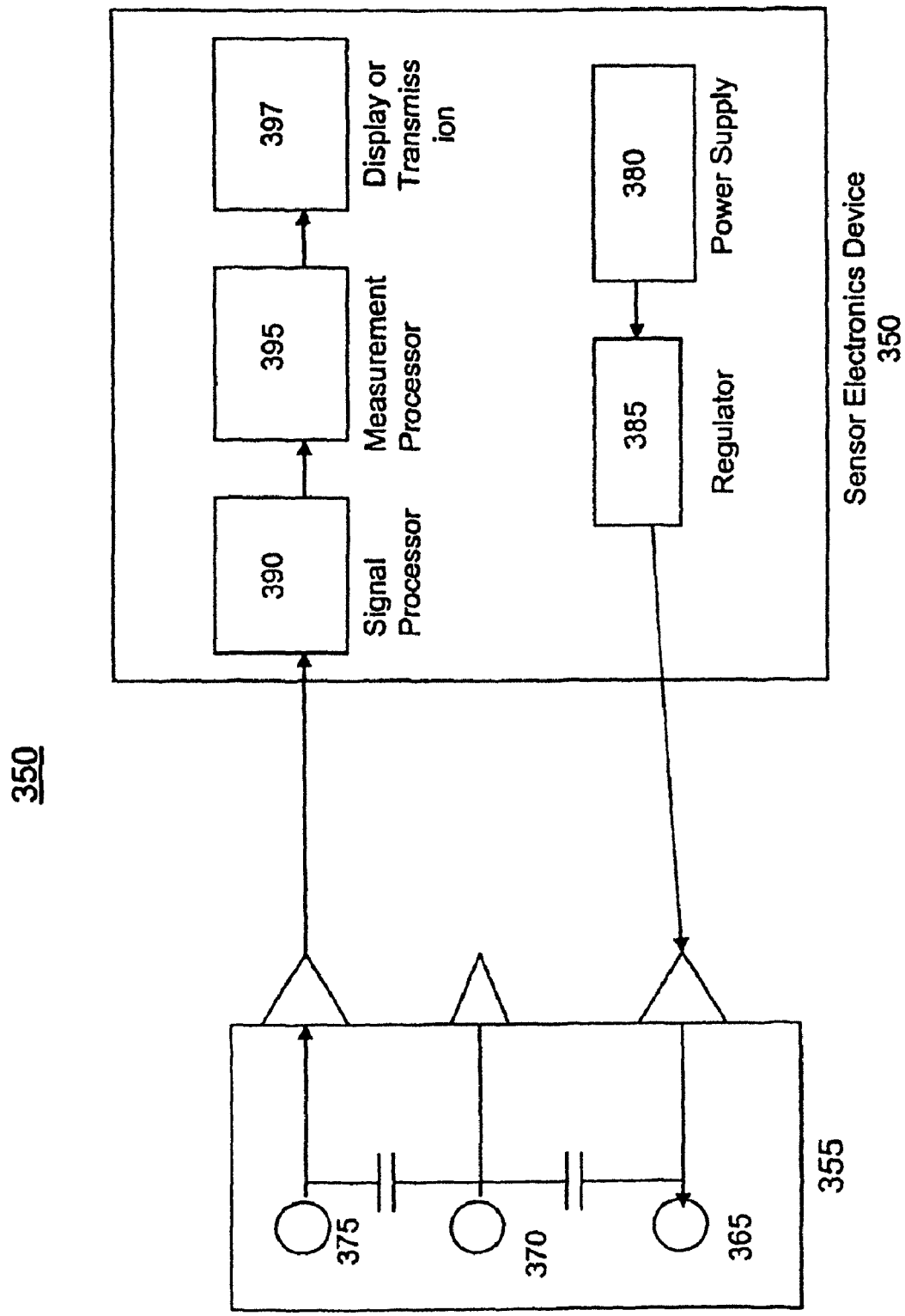
FIG. 3 illustrates a block diagram of a sensor electronics device and a sensor including a plurality of electrodes according to an embodiment of the invention.

FIG. 3 illustrates a block diagram of a sensor electronics device and a sensor including a plurality of electrodes according to an embodiment of the invention. The sensor set or system 350 includes a sensor 355 and a sensor electronics device 360. The sensor 355 includes a counter electrode 365, a reference electrode 370, and a working electrode 375. The sensor electronics device 360 includes a power supply 380, a regulator 385, a signal processor 390, a measurement processor 395, and a display/transmission module 397. The power supply 380 provides power (in the form of either a voltage, a current, or a voltage including a current) to the regulator 385. The regulator 385 transmits a regulated voltage to the sensor 355. In an embodiment of the invention, the regulator 385 transmits a voltage to the counter electrode 365 of the sensor 355.

The sensor 355 creates a sensor signal indicative of a concentration of a physiological characteristic being measured. For example, the sensor signal may be indicative of a blood glucose reading. In an embodiment of the invention utilizing subcutaneous sensors, the sensor signal may represent a level of hydrogen peroxide in a subject. In an embodiment of the invention where blood or cranial sensors are utilized, the amount of oxygen is being measured by the sensor and is represented by the sensor signal. In an embodiment of the invention utilizing implantable or long-term sensors, the sensor signal may represent a level of oxygen in the subject. The sensor signal is measured at the working electrode 375. In an embodiment of the invention, the sensor signal may be a current measured at the working electrode. In an embodiment of the invention, the sensor signal may be a voltage measured at the working electrode.

The signal processor 390 receives the sensor signal (e.g., a measured current or voltage) after the sensor signal is measured at the sensor 355 (e.g., the working electrode). The signal processor 390 processes the sensor signal and generates a processed sensor signal. The measurement processor 395 receives the processed sensor signal and calibrates the processed sensor signal utilizing reference values. In an embodiment of the invention, the reference values are stored in a reference memory and provided to the measurement processor 395. The measurement processor 395 generates sensor measurements. The sensor measurements may be stored in a measurement memory (not pictured). The sensor measurements may be sent to a display/transmission device to be either displayed on a display in a housing with the sensor electronics or to be transmitted to an external device.

The sensor electronics device 350 may be a monitor which includes a display to display physiological characteristics readings. The sensor electronics device 350 may also be installed in a desktop computer, a pager, a television including communications capabilities, a laptop computer, a server, a network computer, a personal digital assistant (PDA), a portable telephone including computer functions, an infusion pump including a display, a glucose sensor including a display, and or a combination infusion pump/glucose sensor. The sensor electronics device 350 may be housed in a blackberry, a network device, a home network device, or an appliance connected to a home network.

Figure 4:
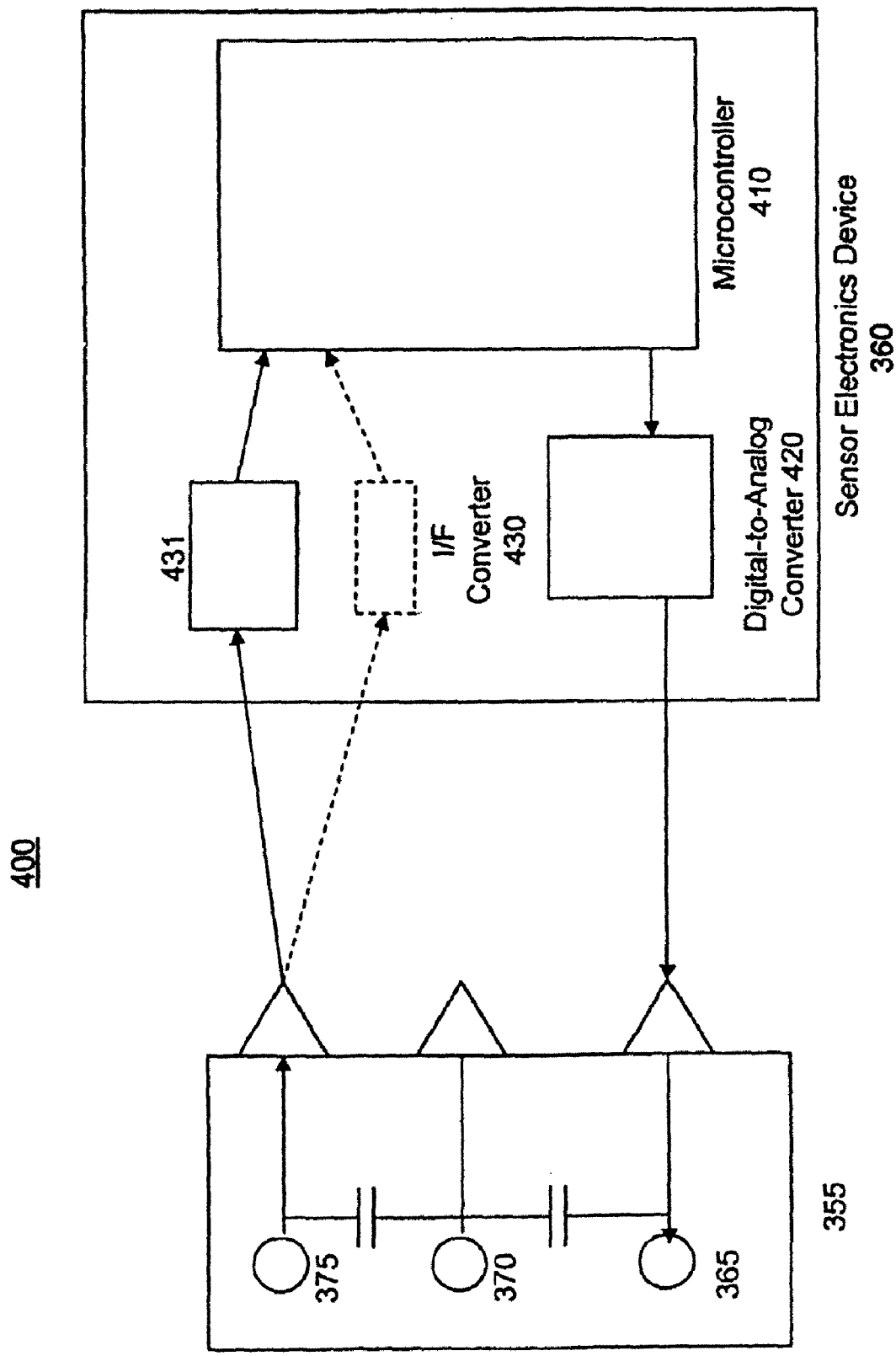
FIG. 4 illustrates an alternative embodiment of the invention including a sensor and a sensor electronics device according to an embodiment of the present invention.

FIG. 4 illustrates an alternative embodiment of the invention including a sensor and a sensor electronics device according to an embodiment of the present invention. The sensor set or sensor system 400 includes a sensor electronics device 360 and a sensor 355. The sensor includes a counter electrode 365, a reference electrode 370, and a working electrode 375. The sensor electronics device 360 includes a microcontroller 410 and a digital-to-analog converter (DAC) 420. The sensor electronics device 360 may also include a current-to-frequency converter (I/F converter) 430.

The microcontroller 410 includes software program code, which when executed, or programmable logic which, causes the microcontroller 410 to transmit a signal to the DAC 420, where the signal is representative of a voltage level or value that is to be applied to the sensor 355. The DAC 420 receives the signal and generates the voltage value at the level instructed by the microcontroller 410. In embodiments of the invention, the microcontroller 410 may change the representation of the voltage level in the signal frequently or infrequently. Illustratively, the signal from the microcontroller 410 may instruct the DAC 420 to apply a first voltage value for one second and a second voltage value for two seconds.

The sensor 355 may receive the voltage level or value. In an embodiment of the invention, the counter electrode 365 may receive the output of an operational amplifier which has as inputs the reference voltage and the voltage value from the DAC 420. The application of the voltage level causes the sensor 355 to create a sensor signal indicative of a concentration of a physiological characteristic being measured. In an embodiment of the invention, the microcontroller 410 may measure the sensor signal (e.g., a current value) from the working electrode. Illustratively, a sensor signal measurement circuit 431 may measure the sensor signal. In an embodiment of the invention, the sensor signal measurement circuit 431 may include a resistor and the current may be passed through the resistor to measure the value of the sensor signal. In an embodiment of the invention, the sensor signal may be a current level signal and the sensor signal measurement circuit 431 may be a current-to-frequency (I/F) converter 430. The current-to-frequency converter 430 may measure the sensor signal in terms of a current reading, convert it to a frequency-based sensor signal, and transmit the frequency-based sensor signal to the microcontroller 410. In embodiments of the invention, the microcontroller 410 may be able to receive frequency-based sensor signals easier than non-frequency-based sensor signals. The microcontroller 410 receives the sensor signal, whether frequency-based or non frequency-based, and determines a value for the physiological characteristic of a subject, such as a blood glucose level. The microcontroller 410 may include program code, which when executed or run, is able to receive the sensor signal and convert the sensor signal to a physiological characteristic value. In an embodiment of the invention, the microcontroller 410 may convert the sensor signal to a blood glucose level. In an embodiment of the invention, the microcontroller 410 may utilize measurements stored within an internal memory in order to determine the blood glucose level of the subject. In an embodiment of the invention, the microcontroller 410 may utilize measurements stored within a memory external to the microcontroller 410 to assist in determining the blood glucose level of the subject.

After the physiological characteristic value is determined by the microcontroller 410, the microcontroller 410 may store measurements of the physiological characteristic values for a number of time periods. For example, a blood glucose value may be sent to the microcontroller 410 from the sensor every second or five seconds, and the microcontroller may save sensor measurements for five minutes or ten minutes of BG readings. The microcontroller 410 may transfer the measurements of the physiological characteristic values to a display on the sensor electronics device 450. For example, the sensor electronics device 450 may be a monitor which includes a display that provides a blood glucose reading for a subject. In an embodiment of the invention, the microcontroller 410 may transfer the measurements of the physiological characteristic values to an output interface of the microcontroller 410. The output interface of the microcontroller 410 may transfer the measurements of the physiological characteristic values, e.g., blood glucose values, to an external device, e.g., such as an infusion pump, a combined infusion pump/glucose meter, a computer, a personal digital assistant, a pager, a network appliance, a server, a cellular phone, or any computing device.

Figure 5:
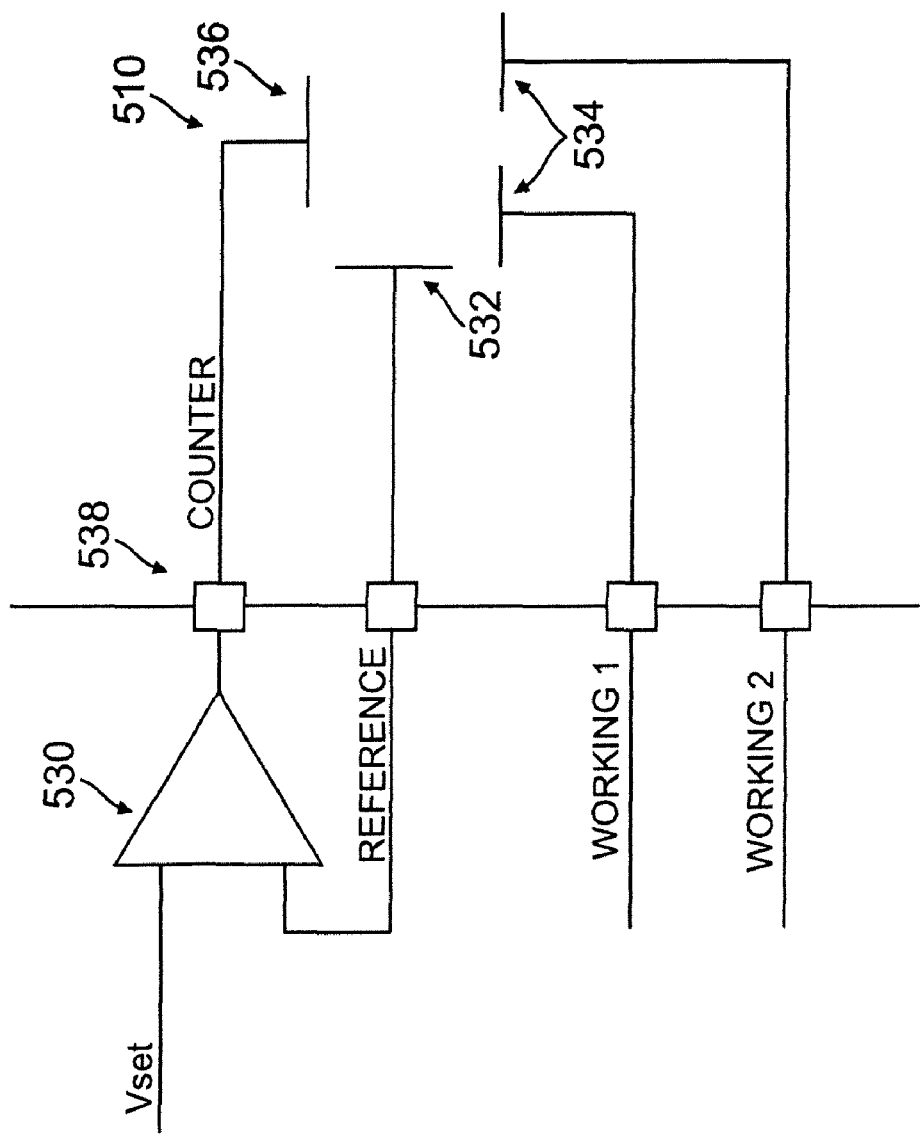
FIG. 5 illustrates an electronic block diagram of the sensor electrodes and a voltage being applied to the sensor electrodes according to an embodiment of the present invention.
Figure 6A:
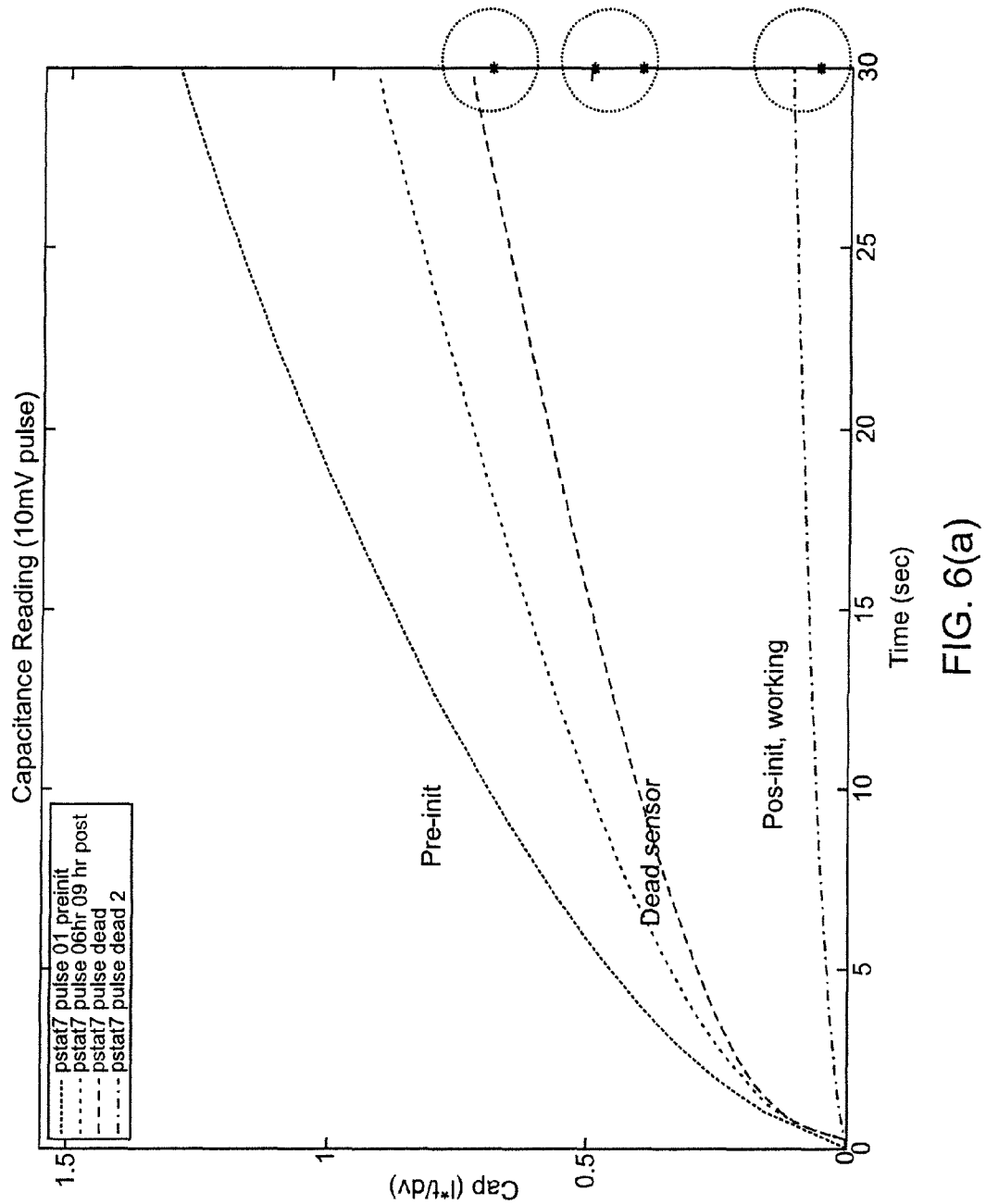
FIG. 6A-6D provide graphs of sensor profiles under various conditions in vitro.
Figure 6B:
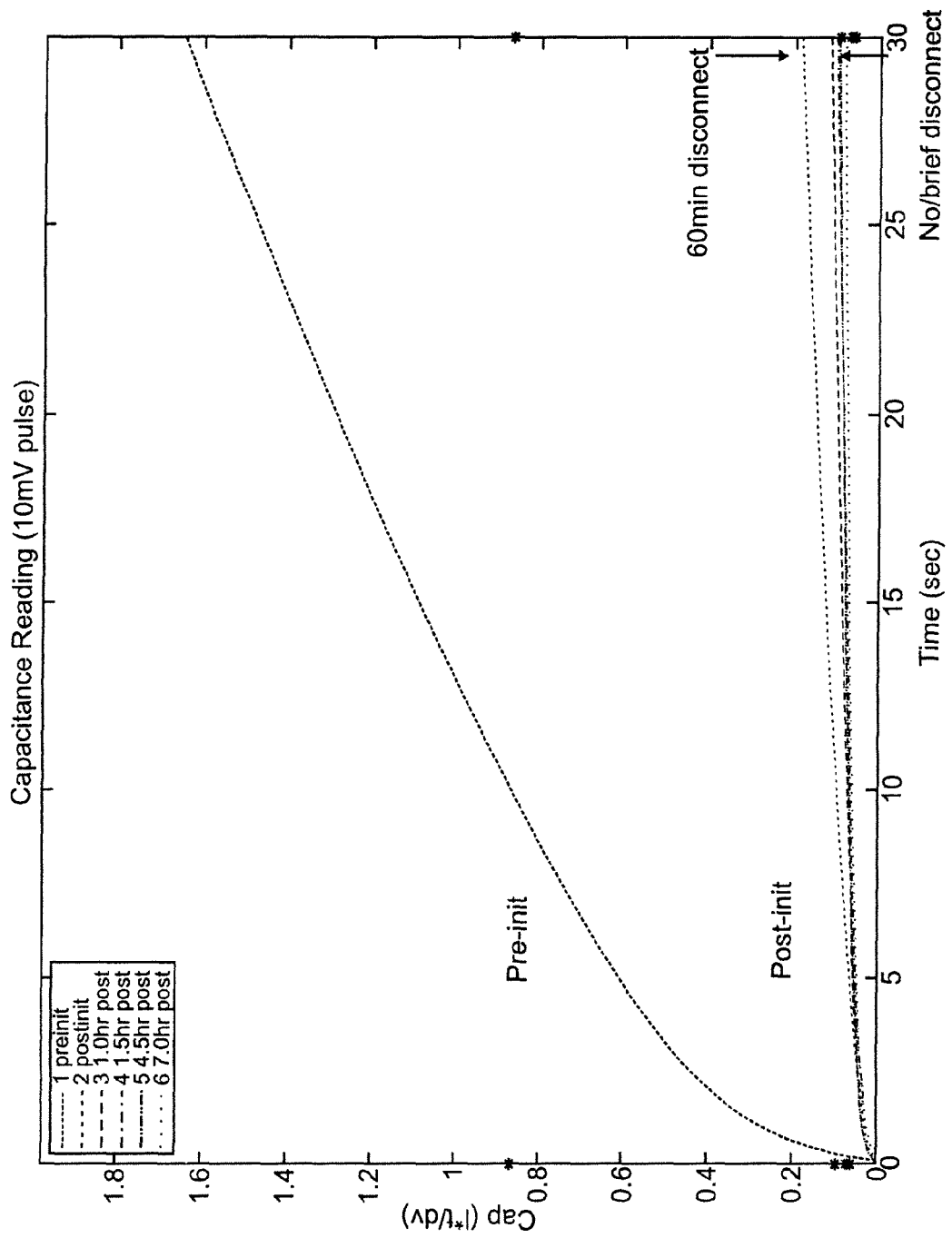
Figure 6C:
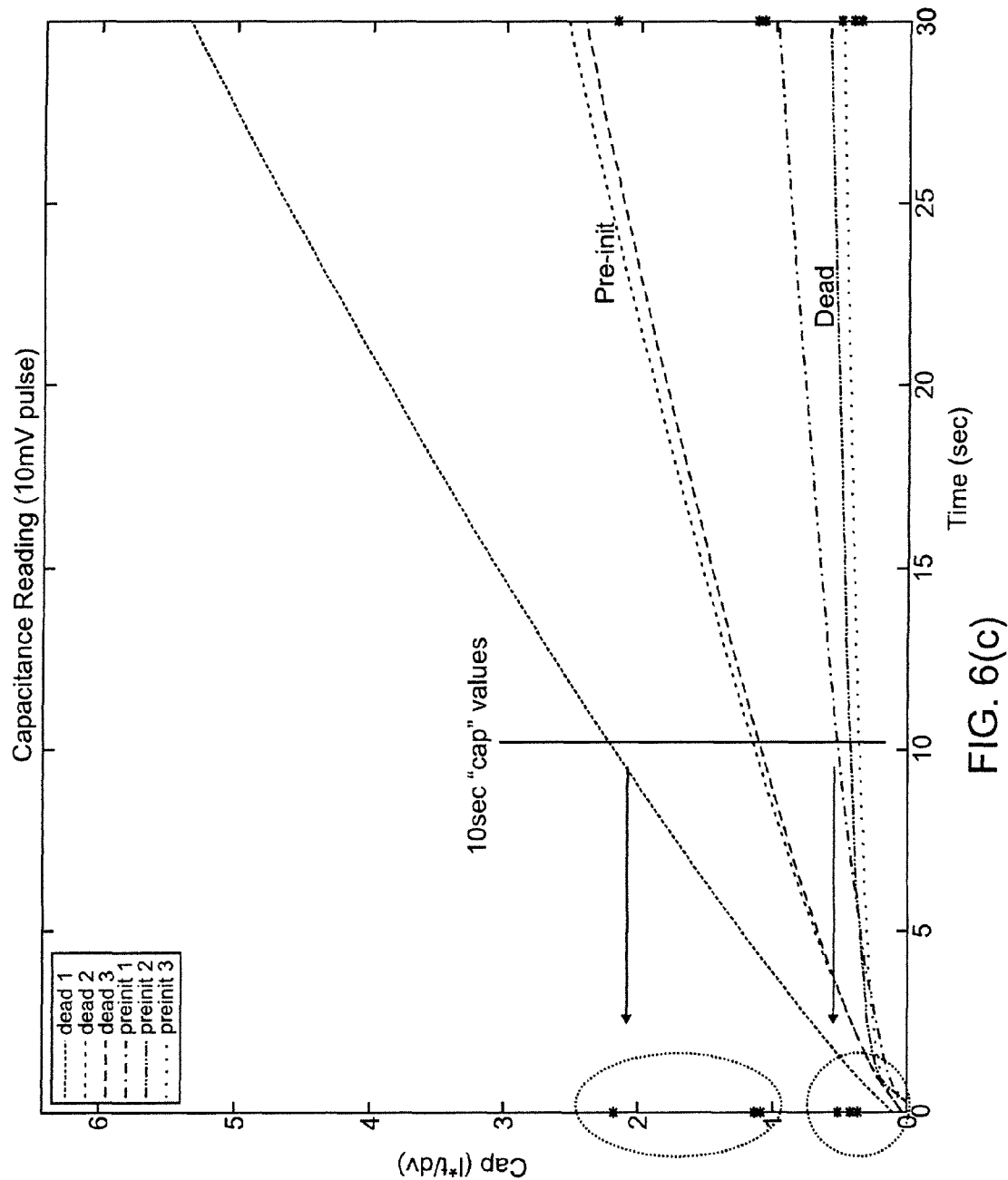
Figure 6D:
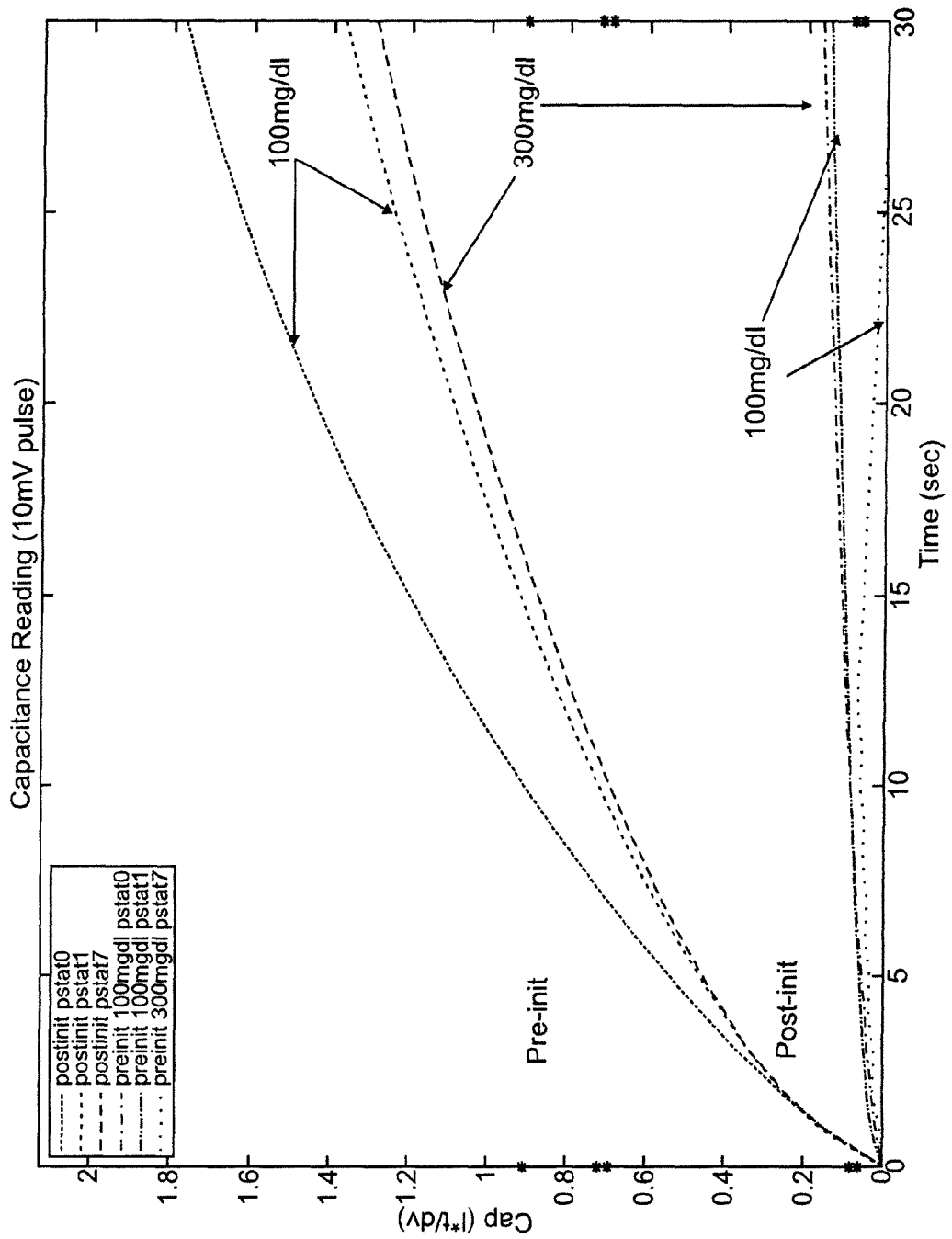
Figure 7:
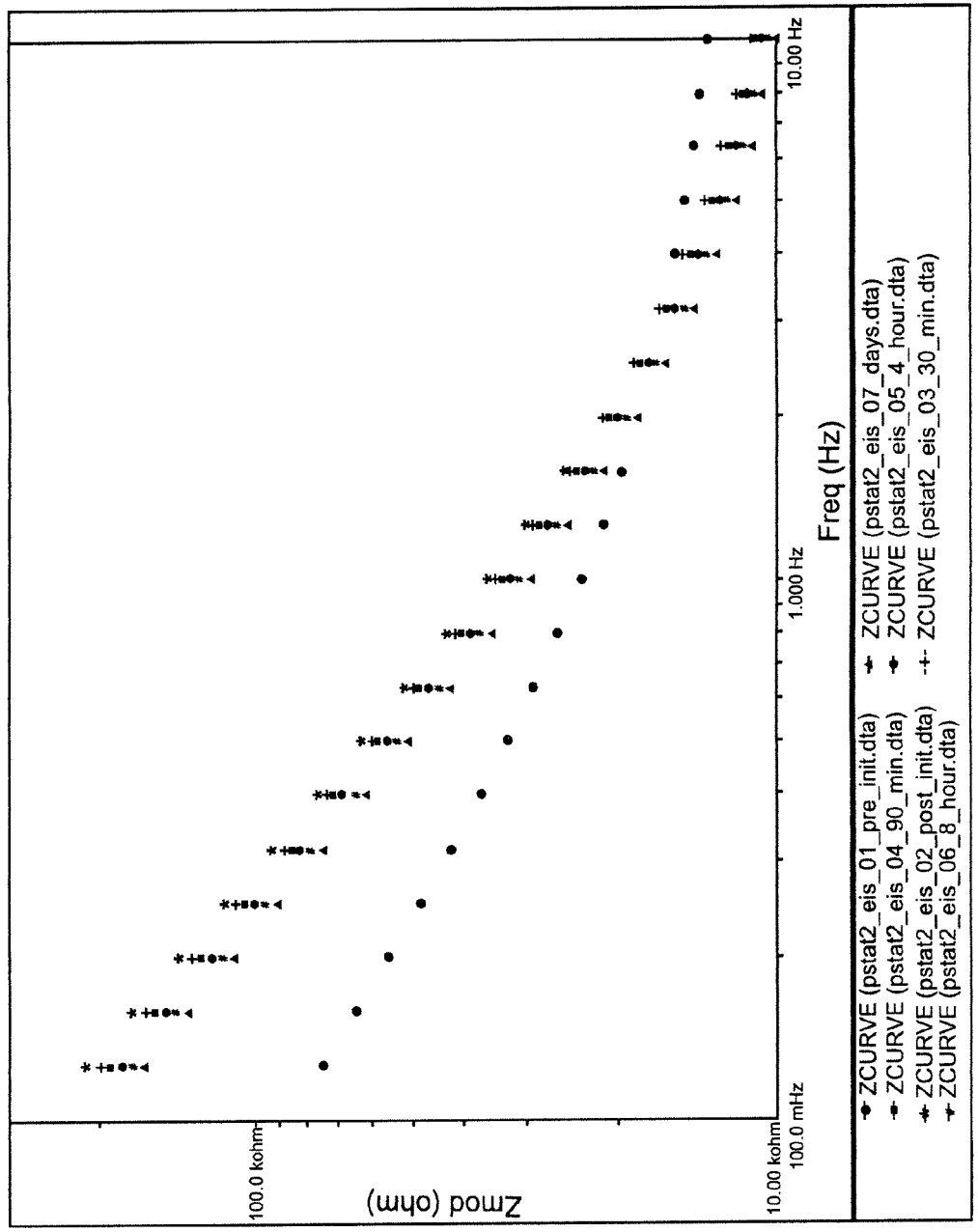
FIG. 7 provides a graph illustrating a 24-hour EIS sampling, SITS.

FIG. 5 illustrates an electronic block diagram of the sensor electrodes and a voltage being applied to the sensor electrodes according to an embodiment of the present invention. In the embodiment of the invention illustrated in FIG. 5, an op amp 530 or other servo controlled device may connect to sensor electrodes 510 through a circuit/electrode interface 538. The op amp 530, utilizing feedback through the sensor electrodes, attempts to maintain a prescribed voltage (what the DAC may desire the applied voltage to be) between a reference electrode 532 and a working electrode 534 by adjusting the voltage at a counter electrode 536. Current may then flow from a counter electrode 536 to a working electrode 534. Such current may be measured to ascertain the electrochemical reaction between the sensor electrodes 510 and the biomolecule of a sensor that has been placed in the vicinity of the sensor electrodes 510 and used as a catalyzing agent. The circuitry disclosed in FIG. 5 may be utilized in a long-term or implantable sensor or may be utilized in a short-term or subcutaneous sensor.

In a long-term sensor embodiment, where a glucose oxidase enzyme is used as a catalytic agent in a sensor, current may flow from the counter electrode 536 to a working electrode 534 only if there is oxygen in the vicinity of the enzyme and the sensor electrodes 10. Illustratively, if the voltage set at the reference electrode 532 is maintained at about 0.5 volts, the amount of current flowing from a counter electrode 536 to a working electrode 534 has a fairly linear relationship with unity slope to the amount of oxygen present in the area surrounding the enzyme and the electrodes. Thus, increased accuracy in determining an amount of oxygen in the blood may be achieved by maintaining the reference electrode 532 at about 0.5 volts and utilizing this region of the current-voltage curve for varying levels of blood oxygen. Different embodiments of the present invention may utilize different sensors having biomolecules other than a glucose oxidase enzyme and may, therefore, have voltages other than 0.5 volts set at the reference electrode.

As discussed above, during initial implantation or insertion of the sensor 510, a sensor 510 may provide inaccurate readings due to the adjusting of the subject to the sensor and also electrochemical byproducts caused by the catalyst utilized in the sensor. A stabilization period is needed for many sensors in order for the sensor 510 to provide accurate readings of the physiological parameter of the subject. During the stabilization period, the sensor 510 does not provide accurate blood glucose measurements. Users and manufacturers of the sensors may desire to improve the stabilization timeframe for the sensor so that the sensors can be utilized quickly after insertion into the subject's body or a subcutaneous layer of the subject.

The invention has a number of embodiments which incorporate one or more of the various elements discussed above. A typical embodiment of the invention is a method of observing a "state" of a sensor (e.g. a measurable and/or quantifiable characteristic of the sensor, for example one or more functional parameters of the sensor, one or more conditions or characteristics of the sensor etc.), the method comprising applying voltage to the sensor, observing a peak instantaneous electrical current of the sensor (e.g. the excitation voltage, namely the nominal voltage required for excitation of a circuit), and observing a total current of the sensor over a period of time for a predetermined frequency so that the state of the sensor is observed. Such methods of the invention can be used to observe a number of sensor parameters. For example, observations of the peak instantaneous electrical current and/or the total current in the sensor over a period of time for a predetermined frequency can be used to estimate sensor impedance magnitude and/or sensor capacitance. Certain embodiments of the invention can be used in manufacturing processes, for example to examine the uniformity of sensors manufactured according to a specific process (e.g. by performing the methods on a plurality of sensors; and then comparing the information so obtained on the state of the plurality of sensors). Such methods can employ those disclosed herein as well as those known in the art and described for example in U.S. Pat. Nos. 7,185,300, 5,751,284, and 5,491,416, the contents of which are incorporated by reference.

Some embodiments of the invention can observe a single phenomena to characterize a state of a sensor such as a peak instantaneous electrical current of the sensor; or alternatively, a total current in the sensor over a period of time for a predetermined frequency. Other embodiments of the invention can observe a combination of such phenomena to characterize a state of a sensor such as a peak instantaneous electrical current of the sensor and in addition a total current in the sensor over a period of time for a predetermined frequency. For example, if an observation of a first phenomena provides in an ambiguous result (e.g. a peak instantaneous electrical current calculated value is too close to the threshold level, or the value indicates a previously used sensor), one can then observe a second phenomena such as a maximum current value (counts/second) over the first 2 second of the pulse (e.g. and use a threshold to determine if the sensor is old or has hydration issues). In such combinatorial embodiments, by for example, checking both the charge capacity and the capacitance one can optimize the chances of identifying sensors functioning outside of desired operating parameters.

There are a variety of ways in which observations on the state or characteristics of a sensor can be obtained. For example, in certain embodiments of the invention, an estimate of sensor capacitance comprises a voltage step analysis using a mathematical formula:

$$C \approx \frac{\sum_{n=1}^{n \leq dt} dI * t_{samp}}{dV}$$

. In this formula, C comprises capacitance, V comprises voltage, dV comprises a controlled voltage step, dt comprises a length of time for analysis, $t_{samp}$ comprises a length of time between samples, and dI comprises a change in current. This formula can be used to provide a "capacitance" estimate, which also includes charge passing through the sensor for an estimation of "impedance magnitude". Typically such observations on the state or characteristics of the sensor are used to obtain information associated with sensor function in vivo, for example the amount or state of sensor hydration, sensor noise, sensor offset, sensor drift or the like.

As noted above, embodiments of the invention can be used to observe sensor offset (i.e. the current not generated in response to glucose). In one illustrative embodiment, the stable-state current response of multiple controlled voltage steps can be used to calculate (by linear regression) the sensor's offset value. In one illustrative embodiment of this, one can observe/sample "stable current" (e.g. capture current at the last second of each step) at voltages such as 535, 545, 555, and 565 mV. One can then calculate a linear regression on the points (y_regression=mx+b). In this embodiment, the difference between the actual current value at 535 and the calculated value from the regression ends up being the offset (o=Isig(535)−y(535)). In a theoretical system, the offset value is what the current value would read if the sensor did not detect any glucose. Consequently, one can subtract this calculated offset from a calibration signal to provide greater accuracy in displaying glucose values. In this context, calculations of linear regression are well known in the art. For example, one simple way to calculate linear regression involves the use of least-squares estimation for linearity, in which the sum of squared error between theoretical and experimental points (current corresponding to each voltage level) is minimized using a set of partial derivatives. The estimator for a least-squares approximation is commonly stated as $\beta=(x'x)^{-1}x'y$. Typically, such computations of linear regression is handled by a mathematical computational program such as MATLAB.

Embodiments of the invention can use a variety of different methodological steps. For example, in certain embodiments of the invention comprise applying a voltage pulse to the sensor. In one illustrative embodiment, the method comprises observing the maximum current value (counts/second) during the initial 2 seconds in response to a voltage pulse applied to the sensor, and then comparing the maximum current value to a predetermined test value. Other embodiments comprise methodological steps such as applying a plurality of voltages and/or currents to the sensor and/or observing current and/or voltage in the sensor over multiple periods of time and/or observing current and/or voltage in the sensor over multiple frequencies. In certain of these embodiments of the invention, a voltage and/or a current applied to the sensor can be in a particular waveform known in the art, for example, a ramped waveform, a sinusoid-shaped waveform, a stepped waveform, a rectangular waveform, a triangular waveform, a trapezoidal waveform, a sawtooth waveform, a logarithmic waveform, a exponential waveform and the like (e.g. other waveforms known in the art).

While a number of the illustrative embodiments of the invention that are disclosed herein outline methods involving the application and manipulation of sensor voltage, the skilled artisan understands that these are provided merely as a non-limiting illustrations of typical embodiments of the invention and that the disclosure provided herein encompasses embodiments of the invention which involve the application, manipulation and measurement of sensor currents. For example, some embodiments of the invention comprise the manipulation of sensor current in order to obtain observations on the state or characteristics of a sensor (e.g. by forcing a current and then measuring the voltage over time) and these methods can be used to obtain information associated with sensor function in vivo, for example the amount or state of sensor hydration, sensor noise, sensor offset, sensor drift or the like (characteristics which can for example, be correlated with sensor impedance). Consequently, in illustrative embodiments of the invention disclosed herein, either: (1) a voltage step (or the like); or (2) a current step (or the like) can be used to obtain estimates on sensor impedance modeled as a series resistor-capacitor (R-C). Those of skill in the art understand that both of these alternative embodiments of the invention involve the basic relationships V=IR for the resistive portion of the impedance and either $C=Q/V$ or $I=C*dV/dt$ for the capacitive portion of the impedance.

One exemplary embodiment of the invention that involves the application and manipulation of sensor current is a method of observing a state of a sensor having a plurality of electrodes, the method comprising: applying a voltage to the sensor; and then measuring a stable-state current (Ibase) produced in response to the voltage applied to the sensor. In this embodiment of the invention, one can then apply the stable-state current so measured to the sensor and then measure the sensor voltage during the application of the stable-state current. In this embodiment of the invention, one can then change the current applied to the sensor to a second current comprising Ibase+deltaI, wherein deltaI comprises the difference between the Ibase and the second current. In this embodiment of the invention, one can then measure sensor voltage during the application of this second current. Following this measurement, one can then observe a first voltage step between the first voltage measurement and the second voltage measurement, a step that results from electrical resistance (R) in the sensor. In this way, the state of the sensor can observed using the application and manipulation of sensor current.

Certain embodiments of the invention that involve the manipulation of sensor current comprise further methodological steps. For example, after the methodological steps discussed in the paragraph above, one can then change applied current applied to the sensor to a third current comprising Ibase+deltaII, wherein deltaII comprises the difference between the Ibase and the third current. In this embodiment of the invention, one can then measure sensor voltage during the application of the third current. Following this measurement, one can then observe a second voltage step between this sensor voltage and the previous voltage measurements; and then calculate a voltage slope (dV/dt) using the multiple voltage step measurements. In such embodiments of the invention, a voltage slope so calculated can then be correlated to a change in sensor capacitance (C) that results from the different currents applied to the sensor. In typical embodiments of the invention, one can calculate resistance (R) in the sensor using a formula R=deltaV/deltaI. In typical embodiments of the invention, one can calculate capacitance (C) in the sensor using a formula C=deltaI/(dV/dt).

Figure 19:
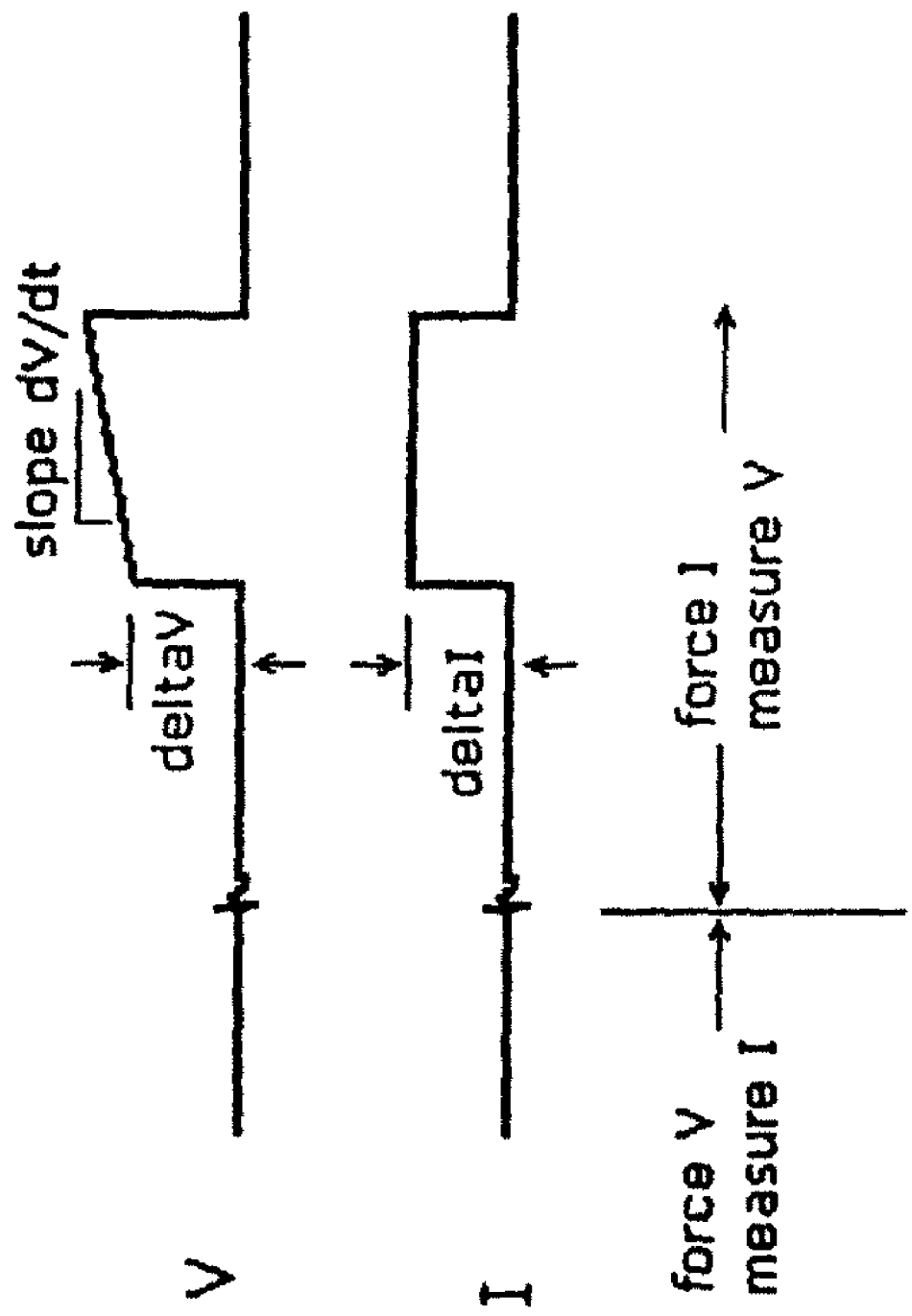
FIG. 19 illustrates aspects of an embodiment of the invention where a current step is used to estimate the impedance modeled as a series R-C. As with the voltage step embodiments disclosed herein, this embodiment considers the basic relationships V=IR for the resistive portion of the impedance and either C=Q/V or I=C*dV/dt for the capacitive portion. In one illustrative way to practice such current step embodiments of the invention is to start with the normally applied stable-state voltage, Vbase (535 mV, for example). In this context, the system can measure the stable-state current, Ibase, under normal operating conditions. Then, the system can switch from forcing voltage to forcing current, using the Ibase measured previously. Then, the current can be stepped to a new value, Ibase+deltaI. This will initially cause a voltage step, deltaV, due to resistance. With a plurality of such steps, a voltage slope can then be obtained, dV/dt (dV is not the same as the initial deltaV step), one related to the charging of the capacitance by the deltaI. The resistance can then be calculated by R=deltaV/deltaI, and the capacitance by C=deltaI/(dV/dt).

In one specific illustrative methodological embodiment of the invention that involves the application of a current step to a sensor in a sensor system, a user can start with a sensor having a normally applied stable-state voltage, Vbase (535 mV, for example). In an initial methodological step in this embodiment of the invention, the sensor system can be used to measure the stable-state current, Ibase, under normal operating conditions. In a subsequent methodological step, the system can switch from forcing voltage to forcing current, using the Ibase measured in the previous step. In some embodiments of the invention, this step can keep the sensor at the same voltage, while in other embodiments the sensor may stabilize at a slightly different voltage (and one can take into account any settling time required for this stabilization, if necessary). In a subsequent methodological step, the current can then be stepped to a new value, Ibase+deltaI. This step will initially result in a voltage step, deltaV, due to resistance. Continuing after that step, there would be a voltage slope, dV/dt (dV is not the same as the initial deltaV step), related to the charging of the capacitance by the deltaI. The resistance would be calculated by R=deltaV/deltaI, and the capacitance would be C=deltaI/(dV/dt). Aspects of this embodiment of the invention are shown in FIG. 19.

The above-noted embodiments of the invention that involve the application and manipulation of sensor current can be used to examine a variety of sensors in a variety of contexts. Optionally for example, the sensor is an electrochemical glucose sensor implanted in vivo and the observations on the state of the sensor provide information on sensor hydration, sensor noise, sensor offset, or sensor drift (e.g. to assess sensor start-up/initialization). Other embodiments of the invention can be used to examine, for example, process variations between batches or lots of sensors made according to identical or non-identical manufacturing processes (e.g. by performing the method on a plurality of sensors made by differing manufacturing processes; and then comparing the information so obtained on the state of the plurality of sensors).

Like the various embodiments of the invention that involve the application and/or manipulation of sensor voltage, the embodiments of the invention that involve the application and manipulation of sensor current also include a sensor system, comprising an implantable sensor, the sensor including a plurality of electrodes; a sensor electronics device, the sensor electronics device capable of being operably connected to the sensor, and the sensor electronics device including: a connection detection device to determine if the sensor electronics device is connected to the sensor and to transmit a connection signal; a power source to supply a regulated voltage; a microprocessor; and a computer-readable program code having instructions, which when executed cause the microprocessor to apply and/or manipulate and/or measure sensor current and/or voltage as disclosed herein.

Similarly, like the various embodiments of the invention that involve the application and/or manipulation of sensor voltage, the embodiments of the invention that involve the application and manipulation of sensor current also include a program code storage device, comprising: a computer-readable medium; a computer-readable program code, stored on the computer-readable medium, the computer-readable program code having instructions, which when executed cause a controller to apply and/or manipulate and/or measure sensor current and/or voltage as disclosed herein.

Embodiments of the invention can be adapted for use with a wide variety of electrochemical sensors such as glucose sensors that comprise glucose oxidase. In one embodiment of the invention, the glucose sensor comprises a base layer, at least three working electrodes disposed on the base layer, a glucose oxidase layer disposed upon the working electrodes, an analyte modulating layer disposed on the glucose oxidase layer, wherein the analyte modulating layer comprises a hydrogel composition, and an adhesion promoting layer disposed between the glucose oxidase layer and the analyte modulating layer. Optionally embodiments of the sensor comprise a plurality of working electrodes and/or counter electrodes and/or reference electrodes (e.g. 3 working electrodes, a reference electrode and a counter electrode), in order to, for example, provide redundant sensing capabilities. Optionally, the plurality of working, counter and reference electrodes are configured together as a unit and positionally distributed on the conductive layer in a repeating pattern of units.

In some embodiments of the invention, an element of the sensor such as an electrode or an aperture is designed to have a specific configuration and/or is made from a specific material and/or is positioned relative to the other elements so as to facilitate a function of the sensor. In one such embodiment of the invention, a working electrode, a counter electrode and a reference electrode are positionally distributed on the base and/or the conductive layer in a configuration that facilitates sensor start up and/or maintains the hydration of the working electrode, the counter electrode and/or the reference electrode when the sensor is placed in contact with a fluid comprising the analyte (e.g. by inhibiting shadowing of an electrode, a phenomena which can inhibit hydration and capacitive start-up of a sensor circuit). Typically such embodiments of the invention facilitate sensor start-up and/or initialization.

Optionally embodiments of the sensor comprise a plurality of working electrodes and/or counter electrodes and/or reference electrodes (e.g. 3 working electrodes, a reference electrode and a counter electrode), in order to, for example, provide redundant sensing capabilities. Certain embodiments of the invention comprise a single sensor. Other embodiments of the invention comprise multiple sensors. Optionally, the plurality of working, counter and reference electrodes are configured together as a unit and positionally distributed on the conductive layer in a repeating pattern of units. In certain embodiments of the invention, the elongated base layer is made from a flexible material that allows the sensor to twist and bend when implanted in vivo; and the electrodes are grouped in a configuration that facilitates an in vivo fluid contacting at least one of working electrode as the sensor twists and bends when implanted in vivo (e.g. so as to facilitate hydration). In some embodiments, the electrodes are grouped in a configuration that allows the sensor to continue to function if a portion of the sensor having one or more electrodes is dislodged from an in vivo environment and exposed to an ex vivo environment.

In an embodiment of the invention that is designed to optimize electrode properties such as hydration, the working electrode, the counter electrode and the reference electrode are positionally distributed on conductive layer in a parallel configuration arranged so that a first electrode is disposed in a region on a first edge of the elongated base layer; a second electrode is disposed in a region on an opposite edge of the elongated base layer; and a third is disposed in a region of the elongated base layer that between the first electrode and the second electrode. Optionally, the working electrode, the counter electrode and the reference electrode are positionally distributed on conductive layer in a configuration arranged so that the working electrode is disposed in a region on a first edge of the elongated base layer; the counter electrode is disposed in a region on an opposite edge of the elongated base layer; and the reference electrode is disposed in a region of the elongated base layer that between the working electrode and the counter electrode. In certain embodiments of the invention, an edge or center of a reference electrode is lined up with an edge or center of the working or counter electrode. In other embodiments of the invention, an edge or center of a reference electrode is offset with an edge or center of the working or counter electrode. In some embodiments of the invention, an electrode matrix is formed in the sensor so as to have no side walls in a manner that further improve hydration of the sensor electrodes. Related embodiments of the invention include methods for using a distributed electrode configuration to facilitate and maintain the hydration and/or initialization properties of various sensor embodiments of the invention.

In certain embodiments of the invention, an element of the sensor such as an electrode or an aperture is designed to have a specific configuration and/or is made from a specific material and/or is positioned relative to the other elements so as to facilitate a function of the sensor. For example, without being bound by a specific theory or mechanism of action, it appears that sensor embodiments (e.g. simple three electrode embodiments) may be more susceptible to local environment changes around a single electrode. For example, a gas bubble on top of or close to a reference or another electrode, and/or a stagnating or semi-stagnating pool of fluid on top of or close to a reference or another electrode may consequently compromises sensor performance. In this context, a distributed electrode configuration appears be advantageous because the distribution of the electrode area allows the sensor to compensate for signal lost to a small local area (e.g. as can occur due to lack of hydration, fluid stagnation, a patient's immune response, or the like). In this context, a system which combines such sensor configurations and the methods for observing sensor parameters (e.g. hydration) provides an optimized system that remedies a number of problems associated with, for example, imperfect sensor hydration.

In certain embodiments of the invention, distributed electrode configurations are used in methods designed to overcome problems with sensors and sensor systems that occur due to lack of hydration (e.g. slow start-up initialization times), fluid stagnation, a patient's immune response, or the like. In addition, embodiments of the invention having distributed electrode configurations can be combined with certain complementary elements disclosed herein so as to further overcome problems that result from a lack of hydration, fluid stagnation, a patient's immune response, or the like (e.g. multiple electrode sensors, voltage pulsing methods etc.).

Various elements of the sensor can be disposed at a certain location in the sensor and/or configured in a certain shape and/or be constructed from a specific material so as to facilitate strength and/or function of the sensor. One embodiment of the invention includes an elongated base comprised of a polyimmide or dielectric ceramic material that facilitates the strength and durability of the sensor. In certain embodiments of the invention, the structural features and/or relative position of the working and/or counter and/or reference electrodes is designed to influence sensor manufacture, use and/or function. Optionally, the sensor is operatively coupled to a constellation of elements that comprise a flex-circuit (e.g. electrodes, electrical conduits, contact pads and the like). One embodiment of the invention includes electrodes having one or more rounded edges so as to inhibit delamination of a layer disposed on the electrode (e.g. an analyte sensing layer comprising glucose oxidase). Related embodiments of the invention include methods for inhibiting delamination of a sensor layer using a sensor embodiments of the invention (e.g. one having one or more electrodes having one or more rounded edges).

Embodiments of the invention include sensor systems such as those comprising an implantable sensor having a plurality of electrodes, a sensor electronics device that is capable of being operably connected to the sensor. Typically, the sensor electronics device includes a connection detection device to determine if the sensor electronics device is connected to the sensor and to transmit a connection signal, a power source to supply a regulated voltage and a microprocessor. Such systems typically include a computer-readable program code having instructions, which when executed cause the microprocessor to apply a voltage to the sensor and then record data on a peak instantaneous electrical current of the sensor in response to the applied voltage as well as record data on a total current of the sensor over a period of time for a predetermined frequency in response to the applied voltage. Optionally in such systems, one or more steps controlled by the microprocessor include applying a plurality of voltages to the sensor and/or applying a voltage pulse to the sensor and/or recording data on a current in the sensor over multiple periods of time and/or recording data on a current in the sensor over multiple frequencies.

Typically the system further comprises a monitor for displaying the data recorded by the microprocessor, wherein the data displayed on the monitor provides information on sensor hydration, sensor noise, sensor offset, sensor drift or the like. Such systems are typically used for example to compare a reading from a test sensor (e.g. a sensor phenomena noted herein such as peak instantaneous current, maximum current value, some combination of these phenomena or the like) with a comparative reading from a control sensor know to be functioning within desired operating parameters and/or a predetermined range of values associated with such desired operating parameters. Optionally in such systems, the implantable sensor is a glucose sensor comprising a base layer, at least three working electrodes disposed on the base layer, a glucose oxidase layer disposed upon the working electrodes, an analyte modulating layer disposed on the glucose oxidase layer; and an adhesion promoting layer disposed between the glucose oxidase layer and the analyte modulating layer. Typically the sensor is implantable in tissue selected from the group consisting of subcutaneous, dermal, sub-dermal, intraperitoneal, and peritoneal tissue.

Yet another embodiment of the invention is a program code storage device comprising a computer-readable medium, a computer-readable program code, stored on the computer-readable medium, the computer-readable program code having instructions, which when executed cause a controller to initiate a series of voltage pulses to be applied to a sensor comprising a plurality of electrodes; and receive a signal from a detection circuit, the signal indicating a peak instantaneous electrical current of the sensor in response to the applied voltage pulses; and a total current of the sensor over a period of time for a predetermined frequency in response to the applied voltage pulses. Optionally the program code storage device includes instructions, which when executed causes the controller to determine the maximum current value (counts/second) during the initial 2 seconds in response to a voltage pulse applied to the sensor, and then compare the maximum current value so determined to a predetermined range of values. In certain embodiments of the invention, the program code storage device includes instructions, which when executed causes the controller to then enable the sensor to measure a physiological characteristic of a patient when the maximum current value is within the predetermined range of values.

Optionally the program codes storage device includes instructions, which when executed cause a controller to initiate a sensor observation routine; and transmit a first signal to a digital-to-analog converter (DAC), the DAC being coupled to an electrode of a sensor, the first signal representative of a observation sequence of voltages that the DAC is to output to the electrode of the sensor, wherein the observation sequence of voltages includes: a first voltage applied for a first time frame; a second voltage applied for a second time frame; and a repeating of the application of the first voltage and the second voltage to the electrodes. In certain embodiments of the invention, the program code storage device includes instructions, when executed cause the controller to repeat the application of the first voltage and the second voltage for a number of iterations. In certain embodiments of the invention, the program code storage device includes instructions, which when executed cause the controller to: change a duration of the first amount of time and a duration of the second amount of time for at least one of the number of iterations. In some embodiments of the invention, the program code storage device includes instructions, which when executed cause the controller to: instruct the DAC to change a magnitude of the first voltage to be applied to the electrode of the sensor at least once during the repeating of the application of the first voltage; and/or instruct the DAC to change a magnitude of the second voltage to be applied to the electrode of the sensor at least once during the repeating of the application of the second voltage.

As noted above, the sensor (or electrodes of a sensor) may be subjected to a number of pulses rather than the application of one pulse followed by the application of another voltage. In such embodiments of the invention, a voltage application device applies a first voltage to an electrode for a first time or time period. In an embodiment of the invention, the first voltage may be a DC constant voltage. This results in an anodic current being generated. In an alternative embodiment of the invention, a digital-to-analog converter or another voltage source may supply the voltage to the electrode for a first time period. The anodic current means that electrons are being driven away from electrode to which the voltage is applied. In an embodiment of the invention, an application device may apply a current instead of a voltage. In an embodiment of the invention where a voltage is applied to a sensor, after the application of the first voltage to the electrode, the voltage regulator may not apply a voltage for a second time, timeframe, or time period. In other words, the voltage application device waits until a second time period elapses. The non-application of voltage results in a cathodic current, which results in the gaining of electrons by the electrode to which the voltage is not applied. The application of the first voltage to the electrode for a first time period followed by the non-application of voltage for a second time period is repeated for a number of iterations. This may be referred to as an anodic and cathodic cycle. In an embodiment of the invention, the number of total iterations of the methodological embodiment is three, i.e., three applications of the voltage for the first time period, each followed by no application of the voltage three times for the second time period. In an embodiment of the invention, the first voltage may be 1.07 volts. In an embodiment of the invention, the first voltage may be 0.535 volts. In an embodiment of the invention, the first voltage may be approximately 0.7 volts.

The result of the repeated application of the voltage and the non-application of the voltage results in the sensor (and thus the electrodes) being subjected to an anodic—cathodic cycle. The anodic—cathodic cycle results in the reduction of electrochemical byproducts, which are generated by a patient's body reacting to the insertion of the sensor or the implanting of the sensor. In an embodiment of the invention, the electrochemical byproducts cause generation of a background current, which results in inaccurate measurements of the physiological parameter of the subject. In an embodiment of the invention, the electrochemical byproduct may be eliminated. Under other operating conditions, the electrochemical byproducts may be reduced or significantly reduced.

In an embodiment of the invention, the first voltage being applied to the electrode of the sensor may be a positive voltage. In an embodiment of the invention, the first voltage being applied may be a negative voltage. In an embodiment of the invention, the first voltage may be applied to a working electrode. In an embodiment of the invention, the first voltage may be applied to the counter electrode or the reference electrode.

In embodiments of the invention, the duration of the voltage pulse and the no application of voltage may be equal, e.g., such as three minutes each. In embodiments of the invention, the duration of the voltage application or voltage pulse may be different values, e.g., the first time and the second time may be different. In an embodiment of the invention, the first time period may be five minutes and the waiting period may be two minutes. In an embodiment of the invention, the first time period may be two minutes and the waiting period (or second timeframe) may be five minutes. In other words, the duration for the application of the first voltage may be two minutes and there may be no voltage applied for five minutes. This timeframe is only meant to be illustrative and should not be limiting. For example, a first timeframe may be two, three, five or ten minutes and the second timeframe may be five minutes, ten minutes, twenty minutes, or the like. The timeframes (e.g., the first time and the second time) may depend on unique characteristics of different electrodes, the sensors, and/or the patient's physiological characteristics.

In embodiments of the invention, more or less than three pulses may be utilized to stabilize the glucose sensor. In other words, the number of iterations may be greater than 3 or less than three. For example, four voltage pulses (e.g., a high voltage followed by no voltage) may be applied to one of the electrodes or six voltage pulses may be applied to one of the electrodes. Illustratively, three consecutive pulses of 1.07 volts (followed by three pulses of no volts) may be sufficient for a sensor implanted subcutaneously. In an embodiment of the invention, three consecutive voltage pulses of 0.7 volts may be utilized. The three consecutive pulses may have a higher or lower voltage value, either negative or positive, for a sensor implanted in blood or cranial fluid, e.g., the long-term or permanent sensors. In addition, more than three pulses (e.g., five, eight, twelve) may be utilized to create the anodic-cathodic cycling between anodic and cathodic currents in any of the subcutaneous, blood, or cranial fluid sensors.

In an embodiment of the invention, the first voltage may be 0.535 volts applied for five minutes, the second voltage may be 1.070 volts applied for two minutes, the first voltage of 0.535 volts may be applied for five minutes, the second voltage of 1.070 volts may be applied for two minutes, the first voltage of 0.535 volts may be applied for five minutes, and the second voltage of 1.070 volts may be applied for two minutes. In other words, in this embodiment, there are three iterations of the voltage pulsing scheme. The pulsing methodology may be changed in that the second timeframe, e.g., the timeframe of the application of the second voltage may be lengthened from two minutes to five minutes, ten minutes, fifteen minutes, or twenty minutes. In addition, after the three iterations are applied in this embodiment of the invention, a nominal working voltage of 0.535 volts may be applied.

The 1.08 and 0.535 volts are illustrative values. Other voltage values may be selected based on a variety of factors. These factors may include the type of enzyme utilized in the sensor, the membranes utilized in the sensor, the operating period of the sensor, the length of the pulse, and/or the magnitude of the pulse. Under certain operating conditions, the first voltage may be in a range of 1.00 to 1.09 volts and the second voltage may be in a range of 0.510 to 0.565 volts. In other operating embodiments, the ranges that bracket the first voltage and the second voltage may have a higher range, e.g., 0.3 volts, 0.6 volts, 0.9 volts, depending on the voltage sensitivity of the electrode in the sensor. Under other operating conditions, the voltage may be in a range of 0.8 volts to 1.34 volts and the other voltage may be in a range of 0.335 to 0.735. Under other operating conditions, the range of the higher voltage may be smaller than the range of the lower voltage. Illustratively, the higher voltage may be in a range of 0.9 to 1.09 volts and the lower voltage may be in a range of 0.235 to 0.835.

In an embodiment of the invention, the first voltage and the second voltage may be positive voltages, or alternatively in other embodiments of the invention, negative voltages. In an embodiment of the invention, the first voltage may be positive and the second voltage may be negative, or alternatively, the first voltage may be negative and the second voltage may be positive. The first voltage may be different voltage levels for each of the iterations. In an embodiment of the invention, the first voltage may be a D.C. constant voltage. In other embodiments of the invention, the first voltage may be a ramp voltage, a sinusoid-shaped voltage, a stepped voltage, or other commonly utilized voltage waveforms. In an embodiment of the invention, the second voltage may be a D.C. constant voltage, a ramp voltage, a sinusoid-shaped voltage, a stepped voltage, or other commonly utilized voltage waveforms. In an embodiment of the invention, the first voltage or the second voltage may be an AC signal riding on a DC waveform. In an embodiment of the invention, the first voltage may be one type of voltage, e.g., a ramp voltage, and the second voltage may be a second type of voltage, e.g., a sinusoid-shaped voltage. In an embodiment of the invention, the first voltage (or the second voltage) may have different waveform shapes for each of the iterations. For example, if there are three cycles in a methodological step, in a first cycle, the first voltage may be a ramp voltage, in the second cycle, the first voltage may be a constant voltage, and in the third cycle, the first voltage may be a sinusoidal voltage.

In an embodiment of the invention, a duration of the first timeframe and a duration of the second timeframe may have the same value, or alternatively, the duration of the first timeframe and the second timeframe may have different values. For example, the duration of the first timeframe may be two minutes and the duration of the second timeframe may be five minutes and the number of iterations may be three. As discussed above, the methodological steps of various embodiments of the invention may include a number of iterations. In embodiments of the invention, during different iterations of the methodological steps, the duration of each of the first timeframes may change and the duration of each of the second timeframes may change. Illustratively, during the first iteration of the anodic-cathodic cycling, the first timeframe may be 2 minutes and the second timeframe may be 5 minutes. During the second iteration, the first timeframe may be 1 minute and the second timeframe may be 3 minutes. During the third iteration, the first timeframe may be 3 minutes and the second timeframe may be 10 minutes.

In an embodiment of the invention, a first voltage of 0.535 volts is applied to an electrode in a sensor for two minutes to initiate an anodic cycle, then a second voltage of 1.07 volts is applied to the electrode to the sensor for five minutes to initiate a cathodic cycle. The first voltage of 0.535 volts is then applied again for two minutes to initiate the anodic cycle and a second voltage of 1.07 volts is applied to the sensor for five minutes. In a third iteration, 0.535 volts is applied for two minutes to initiate the anodic cycle and then 1.07 volts is applied for five minutes. The voltage applied to the sensor is then 0.535 during the actual working timeframe of the sensor, e.g., when the sensor provides readings of a physiological characteristic of a subject.

Shorter duration voltage pulses may be utilized. The shorter duration voltage pulses may be utilized to apply the first voltage, the second voltage, or both. In an embodiment of the present invention, the magnitude of the shorter duration voltage pulse for the first voltage is −1.07 volts and the magnitude of the shorter duration voltage pulse for the second voltage is approximately half of the high magnitude, e.g., −0.535 volts. Alternatively, the magnitude of the shorter duration pulse for the first voltage may be 0.535 volts and the magnitude of the shorter duration pulse for the second voltage is 1.07 volts.

In embodiments of the invention utilizing short duration pulses, the voltage may not be applied continuously for the entire first time period. Instead, in the first time period, the voltage application device may transmit a number of short duration pulses during the first time period. In other words, a number of mini-width or short duration voltage pulses may be applied to the electrodes of the sensors over the first time period. Each mini-width or short duration pulse may a width of a number of milliseconds. Illustratively, this pulse width may be 30 milliseconds, 50 milliseconds, 70 milliseconds or 200 milliseconds. These values are meant to be illustrative and not limiting. In an embodiment of the invention, these short duration pulses are applied to the sensor (electrode) for the first time period and then no voltage is applied for the second time period.

In an embodiment of the invention, each short duration pulse may have the same time duration within the first time period. For example, each short duration voltage pulse may have a time width of 50 milliseconds and each pulse delay between the pulses may be 950 milliseconds. In this example, if two minutes is the measured time for the first timeframe, then 120 short duration voltage pulses may be applied to the sensor. In an embodiment of the invention, each of the short duration voltage pulses may have different time durations. In an embodiment of the invention, each of the short duration voltage pulses may have the same amplitude values. In an embodiment of the invention, each of the short duration voltage pulses may have different amplitude values. By utilizing short duration voltage pulses rather than a continuous application of voltage to the sensors, the same anodic and cathodic cycling may occur and the sensor (e.g., electrodes) is subjected to less total energy or charge over time. The use of short duration voltage pulses utilizes less power as compared to the application of continuous voltage to the electrodes because there is less energy applied to the sensors (and thus the electrodes).

As noted above, embodiments of the innovation include a voltage generation device. The voltage generation or application device typically includes electronics, logic, or circuits, which generate voltage pulses. The sensor electronics device may also include a input device to receive reference values and other useful data. In an embodiment of the invention, the sensor electronics device may include a measurement memory to store sensor measurements. In such embodiments of the invention, the power supply may supply power to the sensor electronics device. The power supply may supply power to a regulator, which supplies a regulated voltage to the voltage generation or application device. In one typically embodiment of the invention, the voltage generation or application device supplies a voltage, e.g., the first voltage or the second voltage, to an input terminal of an operational amplifier. The voltage generation or application device may also supply the voltage to a working electrode of the sensor. Another input terminal of the operational amplifier is coupled to the reference electrode of the sensor. The application of the voltage from the voltage generation or application device to the operational amplifier drives a voltage measured at the counter electrode to be close to or equal the voltage applied at the working electrode. In an embodiment of the invention, the voltage generation or application device could be utilized to apply the desired voltage between the counter electrode and the working electrode. This may occur by the application of the fixed voltage to the counter electrode directly.

In some embodiments of the invention, the voltage generation device generates a first voltage that is to be applied to the sensor during a first timeframe. The voltage generation device then transmits this first voltage to an op amp, which drives the voltage at a counter electrode of the sensor to the first voltage.

In an embodiment of the invention, the voltage generation device also could transmit the first voltage directly to the counter electrode of the sensor. In one embodiment of the invention, the voltage generation device does not transmit the first voltage to the sensor for a second timeframe. In other words, the voltage generation device is turned off or switched off. The voltage generation device may be programmed to continue cycling between applying the first voltage and not applying a voltage for either a number of iterations or for a predetermined timeframe, e.g., for twenty minutes. Typically in such embodiments, the voltage regulator transfers the regulated voltage to the voltage generation device. A control circuit controls the closing and opening of a switch. If the switch is closed, the voltage is applied. If the switch is opened, the voltage is not applied. The timer provides a signal to the control circuit to instruct the control circuit to turn on and off the switch. The control circuit includes logic which can instruct the circuit to open and close the switch a number of times (to match the necessary iterations). In an embodiment of the invention, the timer may also transmit a signal to identify that the sequence is completed, i.e. that a predetermined timeframe has elapsed.

In an embodiment of the invention, the voltage generation device generates a first voltage for a first timeframe and generates a second voltage for a second timeframe for example by using a two-voltage switch. Illustratively, if the first switch position is turned on or closed by a timer instructing the control circuit, then the voltage generation device generates a first voltage for the first timeframe. After the first voltage has been applied for the first timeframe, timer sends a signal to the control circuit indicating the first timeframe has elapsed and the control circuit directs the switch to move to the second position. When the switch is at the second position, the regulated voltage is directed to a voltage step-down or buck converter to reduce the regulated voltage to a lesser value. The lesser value is then delivered to the op amp for the second timeframe. After the timer has sent a signal to the control circuit that the second timeframe has elapsed, then the control circuit moves the switch back to the first position.

The voltage application device may include a control device, a switch, a sinusoid generation device, a ramp voltage generation device, and a constant voltage generation device. In other embodiments of the invention, the voltage application may generate an AC wave on top of a DC signal or other various voltage pulse waveforms. In an embodiment of the invention, the control device may cause the switch to move to one of the three voltage generation systems (sinusoid, ramp, and/or constant DC). This results in each of the voltage regulation systems generating the identified voltage waveform. Under certain operating conditions, e.g., where a sinusoidal pulse is to be applied for three pulses, the control device may cause the switch to connect the voltage from the voltage regulator to the sinusoid voltage generator in order for the voltage application device to generate a sinusoidal voltage. Under other operating conditions, e.g., when a ramp voltage is applied to the sensor as the first voltage for a first pulse of three pulses, a sinusoid voltage is applied to the sensor as the first voltage for a second pulse of the three pulses, and a constant DC voltage is applied to the sensor as the first voltage for a third pulse of the three pulses, the control device may cause the switch, during the first timeframes in the anodic/cathodic cycles, to move between connecting the voltage from the voltage generation or application device to the ramp voltage generation system, then to the sinusoidal voltage generation system, and then to the constant DC voltage generation system. In this embodiment of the invention, the control device may also be directing or controlling the switch to connect certain ones of the voltage generation subsystems to the voltage from the regulator 385 during the second timeframe, e.g., during application of the second voltage.

Embodiments of the invention may include a microcontroller, a digital-to-analog converter (DAC), an op amp, and a sensor signal measurement circuit. In an embodiment of the invention, the sensor signal measurement circuit may be a current-to-frequency (I/F) converter. In some embodiments of the invention, software or programmable logic in the microcontroller provides instructions to transmit signals to the DAC, which in turn instructs the DAC to output a specific voltage to the operational amplifier. The microcontroller may also be instructed to output a specific voltage to the working electrode. As discussed above, the application of the specific voltage to operational amplifier and the working electrode may drive the voltage measured at the counter electrode to the specific voltage magnitude. In other words, the microcontroller outputs a signal, which is indicative of a voltage or a voltage waveform that is to be applied to the sensor (e.g., the operational amplifier coupled to the sensor). In an alternative embodiment of the invention, a fixed voltage may be set by applying a voltage directly from the DAC between the reference electrode and the working electrode. A similar result may also be obtained by applying voltages to each of the electrodes with the difference equal to the fixed voltage applied between the reference and working electrode. In addition, the fixed voltage may be set by applying a voltage between the reference and the counter electrode. Under certain operating conditions, the microcontroller may generates a pulse of a specific magnitude which the DAC understands represents that a voltage of a specific magnitude is to be applied to the sensor. After a first timeframe, the microcontroller (via the program or programmable logic) outputs a second signal, which either instructs the DAC to output no voltage or to output a second voltage. The microcontroller, after the second timeframe has elapsed, then repeats the cycle of sending the signal indicative of a first voltage to apply, (for the first timeframe) and then sending the signal to instruct no voltage is to be applied or that a second voltage is to be applied (for the second timeframe).

Under other operating conditions, the microcontroller may generate a signal to the DAC, which instructs the DAC to output a ramp voltage. Under other operating conditions, the microcontroller may generate a signal to the DAC, which instructs the DAC to output a voltage simulating a sinusoidal voltage. These signals could be incorporated into any of the pulsing methodologies discussed above in the preceding paragraph or earlier in the application. In an embodiment of the invention, the microcontroller may generate a sequence of instructions and/or pulses, which the DAC receives and understands to mean that a certain sequence of pulses is to be applied. For example, the microcontroller may transmit a sequence of instructions (via signals and/or pulses) that instruct the DAC to generate a constant voltage for a first iteration of a first timeframe, a ramp voltage for a first iteration of a second timeframe, a sinusoidal voltage for a second iteration of a first timeframe, and a squarewave having two values for a second iteration of the second timeframe.

The microcontroller may include programmable logic or a program to continue this cycling for a timeframe or for a number of iterations. Illustratively, the microcontroller may include counting logic to identify when the first timeframe or the second timeframe has elapsed. Additionally, the microcontroller may include counting logic to identify that a timeframe has elapsed. After any of the preceding timeframes have elapsed, the counting logic may instruct the microcontroller to either send a new signal or to stop transmission of a signal to the DAC.

The use of the microcontroller allows a variety of voltage magnitudes to be applied in a number of sequences for a number of time durations. In an embodiment of the invention, the microcontroller may include control logic or a program to instruct the digital-to-analog converter to transmit a voltage pulse having a magnitude of approximately 1.0 volt for a first time period of 1 minute, to then transmit a voltage pulse having a magnitude of approximately 0.5 volts for a second time period of 4 minutes, and to repeat this cycle for four iterations. In an embodiment of the invention, the microcontroller may be programmed to transmit a signal to cause the DAC to apply the same magnitude voltage pulse for each first voltage in each of the iterations. In an embodiment of the invention, the microcontroller may be programmed to transmit a signal to cause the DAC to apply a different magnitude voltage pulse for each first voltage in each of the iterations. In this embodiment of the invention, the microcontroller may also be programmed to transmit a signal to cause the DAC to apply a different magnitude voltage pulse for each second voltage in each of the iterations. Illustratively, the microcontroller may be programmed to transmit a signal to cause the DAC to apply a first voltage pulse of approximately one volt in the first iteration, to apply a second voltage pulse of approximately 0.5 volts in the first iteration, to apply a first voltage of 0.7 volts and a second voltage of 0.4 volts in the second iteration, and to apply a first voltage of 1.2 and a second voltage of 0.8 in the third iteration.

The microcontroller may also be programmed to instruct the DAC to provide a number of short duration voltage pulses for a first timeframe. In this embodiment of the invention, rather than one voltage being applied for the entire first timeframe (e.g., two minutes), a number of shorter duration pulses may be applied to the sensor. In this embodiment, the microcontroller may also be programmed to program the DAC to provide a number of short duration voltage pulses for the second timeframe to the sensor. Illustratively, the microcontroller may send a signal to cause the DAC to apply a number of short duration voltage pulses where the short duration is 50 milliseconds or 100 milliseconds. In between these short duration pulses the DAC may apply no voltage or the DAC may apply a minimal voltage. The DAC may cause the microcontroller to apply the short duration voltage pulses for the first timeframe, e.g., two minutes. The microcontroller may then send a signal to cause the DAC to either not apply any voltage or to apply the short duration voltage pulses at a magnitude of a second voltage for a second timeframe to the sensor, e.g., the second voltage may be 0.75 volts and the second timeframe may be 5 minutes. In an embodiment of the invention, the microcontroller may send a signal to the DAC to cause the DAC to apply a different magnitude voltage for each of short duration pulses in the first timeframe and/or in the second timeframe. In an embodiment of the invention, the microcontroller may send a signal to the DAC to cause the DAC to apply a pattern of voltage magnitudes to the short durations voltage pulses for the first timeframe or the second timeframe. For example, the microcontroller may transmit a signal or pulses instructing the DAC to apply thirty 20 millisecond pulses to the sensor during the first timeframe. Each of the thirty 20 millisecond pulses may have the same magnitude or may have a different magnitude. In this embodiment of the invention, the microcontroller may instruct the DAC to apply short duration pulses during the second timeframe or may instruct the DAC to apply another voltage waveform during the second timeframe.

Although the embodiments discussed above disclose the application of a voltage, a current may also be applied to the sensor in certain embodiments of the invention. Illustratively, a first current may be applied during a first timeframe to initiate an anodic or cathodic response and a second current may be applied during a second timeframe to initiate the opposite anodic or cathodic response. The application of the first current and the second current may continue for a number of iterations or may continue for a predetermined timeframe. In an embodiment of the invention, a first current may be applied during a first timeframe and a first voltage may be applied during a second timeframe. In other words, one of the anodic or cathodic cycles may be triggered by a current being applied to the sensor and the other of the anodic or cathodic cycles may be triggered by a voltage being applied to the sensor. As described above, a current applied may be a constant current, a ramp current, a stepped pulse current, or a sinusoidal current. Under certain operating conditions, the current may be applied as a sequence of short duration pulses during the first timeframe.

The present invention is further detailed in the following Examples, which are offered by way of illustration and are not intended to limit the invention in any manner. All patent and literature references cited in the present specification are hereby incorporated by reference in their entirety. For purposes of clarity, certain techniques that are well known and well described in the art are reproduced herein.

EXAMPLES

Example 1

Application of an Instantaneous Voltage Step Across the Working Electrode in Order to Obtain Estimations of Electrode Impedance Electrochemical Impedance Spectroscopy In spectroscopic analysis, a spectrum of wavelengths applied to a sample generates a corresponding response specific to its material properties. Data from an unknown sample can be analyzed with respect to calibrated response profiles in an attempt to guess at its material properties. In the case of electrochemical impedance spectroscopy, the complex impedance of an object at different frequencies will vary depending on its size (i.e. low vs. high surface area) and material content (i.e. platinum vs. gold).

In potentiometric EIS, two or more leads are connected across a sample while the potential at one end is cycled through various frequencies with a set peak-to-peak voltage. The resulting current between two leads is recorded. Using excitation voltage and reading current over a full period (or multiple periods) for a particular frequency, one is able to extract the complex impedance (magnitude and phase).

Scanning across multiple frequencies and comparing between samples, the difference between a working and non-working sensor based on changes in impedance over time is able to be detected. It is inferred that this same technique may be applied to 1) determine differences between sensors that have been initialized vs. non-initialized, 2) be a possible indicator for changes in membrane impedance due to biofouling, or 3) estimate projected sensor lifetime.

DEFINITIONS

CF—Calibration Factor
dt—Time elapsed after voltage step (sec)
dV—Change in voltage (V)
EIS—Electrochemical Impedance Spectroscopy
I, dI—Current (amps), or the change in current amplitude
PTS—Prototype Test System
Q—Charge (C)
RMS—Root Mean Squared
SITS—Short-term Sensor In-vitro Test System
T_samp—Sampling time (1/freq)
Typical Equipment and Supplies:
Gamry MultEchem 8 Electrochemistry System
Gamry Echem Analyst Software
MATLAB 7.6.0 (R2008a)

Figure 8:
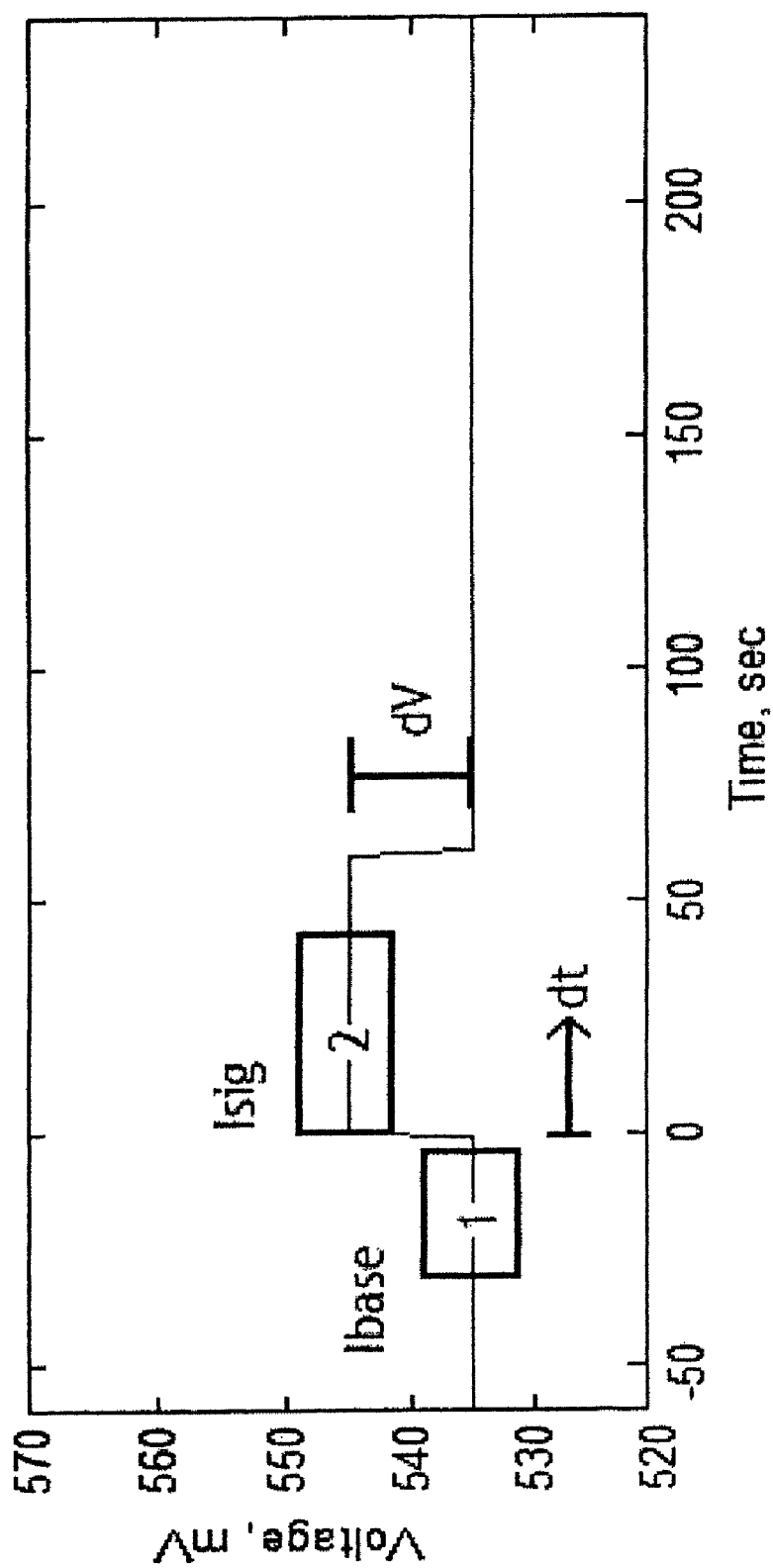
FIG. 8 provides a graph illustrating a transient 10 mV voltage pulse.

As disclosed herein, experiments have been conducted using a Gamry 8-channel potentiostat system to analyze the complex impedance of sensors both in vivo and in vitro. As shown in FIG. 8, EIS samples were obtained between 100 KHz and 0.1 Hz using a mV (RMS) AC pulse overlaying a 535 mV DC static potential. Samples were taken before sensor initialization, post-initialization, and several time points following.

Echem Analyst software also allows the user to fit data to a complex impedance model via the Levenberg-Marquardt method for solving non-linear problems. From a small sample size (n=3), the best fit equivalent model for a working sensor was described as a series RC circuit with R=11 KOhm and C=4.4 uF.

Using this model, a high magnitude impedance (above 100 KOhm) and close to pi/2 phase (indicating a large capacitive component to the impedance) was expected to be observed. Before initialization, the capacitance and resistance appear to be significantly higher; after initialization the values appear to settle in with limited change in impedance over the next few days.

Voltage Step Theory

While EIS is a reliable tool in differentiating between sensors, obtaining impedance may not be necessary if the diagnostic frequencies of interest are composed of near-DC frequencies (0.100 Hz). By inducing a small transient voltage step, the resulting instantaneous current profile could be analyzed as a method to extrapolate the imaginary impedance. It is thought that the capacitive elements (imaginary component of impedance) of the sensor are providing the bulk of the changes to the EIS profile, obtaining capacitance measurements provides all the information needed.

$$C = \frac{Q}{V} = \frac{\int I * dt}{\text{Voltage}} \quad \text{Equation 1}$$

$$C \approx \frac{\sum_{n=1}^{n \leq dt} dI * t_{samp}}{dV} \quad \text{Equation 2}$$

By controlling the change in voltage (dV), controlling time (dt), and monitoring changes in current (dI) over a number of samples (n) an estimation of the capacitance at the sensor surface is obtained. The sampling time (t same) translates the sum of current into charge stored in a given period of time $dt = n * t_{samp}$.

In FIG. 8, a voltage step is performed for 60 seconds during which dV is controlled (10 mV), dt is controlled (1-60 sec), and dI is calculated from the difference between Isig and Ibase (instantaneous current vs. pre-step current).

By sampling data well beyond the RC time constant, the component of real impedance is also added to the measurement When data is collected, any analysis will reflect values of complex impedance, though a large portion of the impedance will be made up of capacitive elements—in this document, the terms capacitance and complex impedance are used interchangeably.

There are several issues that may be of concern when using a voltage-pulse (or current-pulse) to determine capacitance. The sensor current will track with any change in interstitial glucose/hydrogen peroxide concentration (as well as interfering compounds, i.e. acetaminophen). As a result, any changes in voltage will scale current values depending on the transient systemic glucose concentration at the time. The capacitance measurement obtained in 100 mg/dl (standard) glucose concentration can be smaller than one obtained in 300 mg/dl (elevated glucose level).

A scale factor for the capacitance measurement based on the current values obtained before a pulse is initiated can solve this problem. Effectively, analyzing a properly scaled, differential capacitance measurement can overcome any possible errors due to varying glucose concentration (assume constant glucose concentration over one sample). It may be possible to avoid using a scale factor and rely on differential current to calculate our stored charge variable.

A second concern is in the identification of sensor failures. In general, a sensor enters failure mode with either delamination or a general loss of sensitivity. Delamination is characterized by a significant increase in signal noise (may be easier to identify based on current stability), whereas loss of sensitivity refers to instances in which the sensor no longer follows with glucose concentration.

It has been confirmed via EIS that impedance magnitude will change with membrane delamination. However, changes in impedance (particularly, increases) may be difficult to detect: bad sensors may be indistinguishable from the low capacitance of initialized, working sensor. Sensors that lose their sensitivity may or may not have changes in their complex impedance—it remains to be seen the degree (if at all) of difference in capacitance between working and failed sensors.

In typical experiments, sensors are inserted within a flow system simulating interstitial fluid in the body and left unpowered until glucose concentration is confirmed (via YSI) to be stable at approximately 100 mg/dl. Individual sensors will be powered by independent potentiostats of a Gamry E-Chem system. Further modifications to glucose concentration, temperature, or gas content will be performed depending on experimental requirements.

Results and Discussion:
Preliminary Experimental Data

Figure 9:
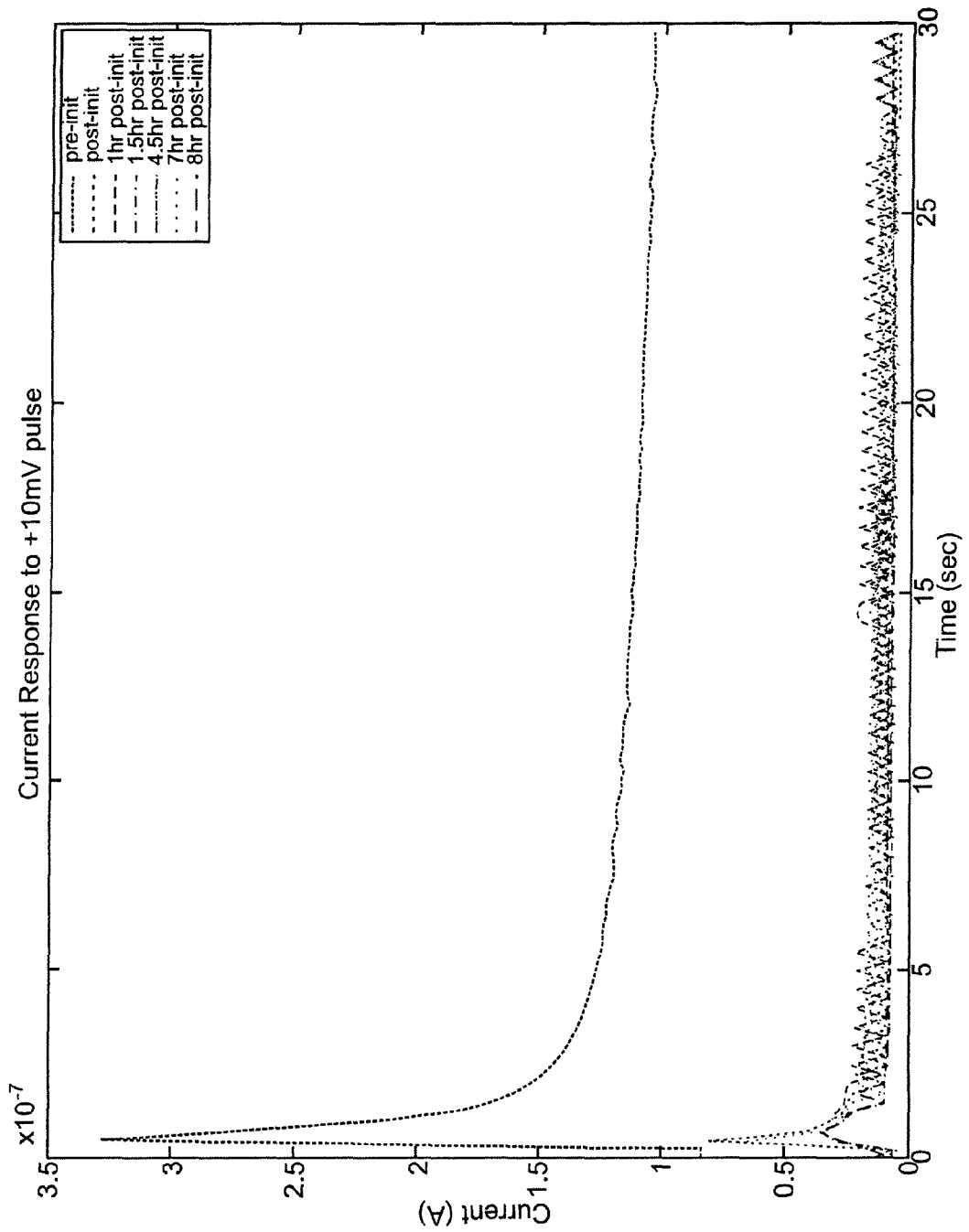
FIG. 9 provides a graph illustrating a current response, 10 mV pulse in SITS.

As shown for example in FIG. 9, preliminary results indicate that both Isig and Capacitance are useful alternatives to the implementation of a full-featured EIS chip. In the first experiment, pulsing and EIS samples were obtained over a 9 hour period.

The current response of a pre-initialized sensor has different characteristics from all of the other samples conducted after initialization. Over the course of 8-9 hours, we observe negligble current drift compared to the response profile for a unused, non-initialized sensor. We can take the value of sensor current at time t=10 after a voltage pulse and use that for a diagnostic check for sensors in the initialization state.

Figure 10:
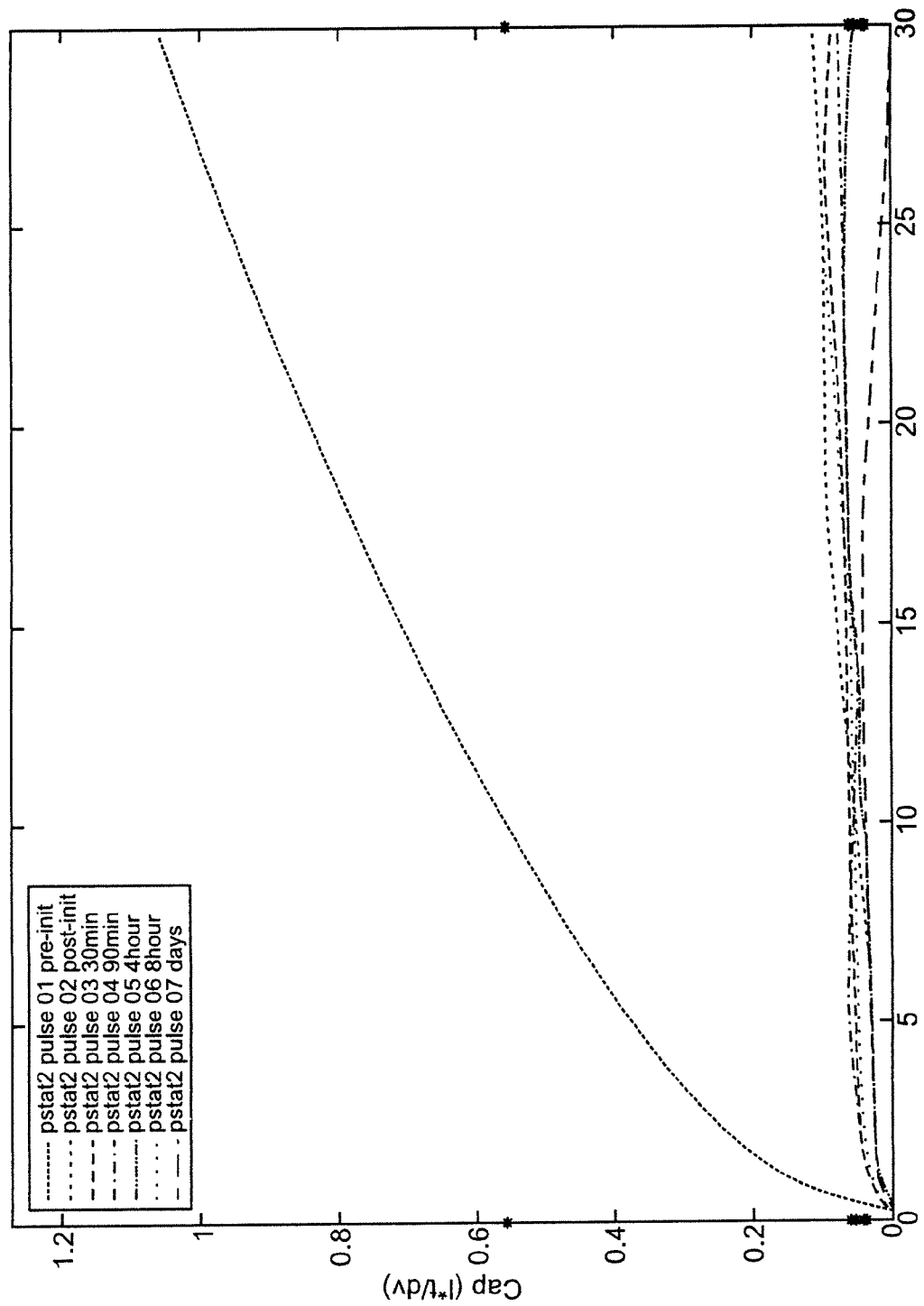
FIG. 10 provides a graph illustrating capacitance, 10 mV step, SITS.

Capacitance was calculated as described in sections 7.3 and 9.2.3. The results are uniform across multiple sensors: there is a significant difference in measured capacitance between pre- and post-initialized sensors. Additionally, the post-initialization samples show very little drift (system noise) between measurements over time. In FIG. 10, the capacitance reading at 10 sec is marked on the left and right edges in red. The lone high mark represents capacitance at pre-initialization levels. The other grouping comes from the various samples taken at different time points after initialization. A lack of failing sensor data limits what one can determine from such demonstrations, but alternative embodiments can be used to examine capacitance in sensors that have become non-sensitive to changes in glucose concentration—whether by membrane delamination or in our case, enzyme degradation.

One point to note is that partially hydrated sensors could potentially be improperly identified as initialized sensors. A mostly dry sensor would have high impedance (low current), indicative of a sensor that has already gone through initialization. This misrepresentation of sensor state may be overlooked for our purposes: sensors should not be initialized until they are fully hydrated. However, it may be difficult to categorize or separate initialized sensors from those that are only partially hydrated.

Though glucose was controlled (a constant 100 mg/dl) over time, in normal testing and operation glucose concentration will drift anywhere between 40 mg/dl and 400 mg/dl. The resulting sensor response would drive changes in Isig and capacitance, possibly pushing post-init pulse sampling into the range of pre-init samples. EIS sampling at different glucose concentrations has not indicated any significant impedance drift.

Concentration Dependence Test

In typical experiments, sensors inserted into PTS were initialized in two separate concentrations of glucose: 107.3 mg/dl and 289.7 mg/dl (100 or 300 mg/dl, respectively). Pre-initialized samples were taken after running the sensor at 535 mV for 5 minutes; initialized data was sampled 9 hours after the completion of the initialization sequence. The experimental sequence taken here was the same as in 10.1: running over-potential of 535 mV with intermediate 60 sec pulsing of 10 mV to 545 mV. By comparing the current and capacitance profiles of identically produced sensors, we may determine whether or not the environmental glucose concentration will significantly affect our step response test.

Response profiles look very similar between sensors and across varying glucose concentration. In general, current amplitude after a pulse in pre-initialized sensors (~60 nA) is approximately 7-times higher in amplitude than the response in post-initialization sensors (~10 nA). Our "capacitance" measurement involves a summation of the current (charge buildup), so it is expected that the capacitance response will provide similar results. In fact, uniform results across multiple sensors, with new sensors having an order of magnitude higher capacitance than sensors which have already been initialized is observed.

The data provides evidence that the concentration of glucose does not affect the results of the differential pulse analysis technique.

Similarly, EIS samples taken at the same time-points were not significantly affected by changes in glucose concentration. Using 0.1 Hz excitation, impedance readings differ significantly between new and used sensors ($\Delta R \geq 100$ k, $\Delta \phi \geq 15°$).

Dead Sensor Test

In this experiment, sensors were inserted in PTS, initialized, and run for several hours in the 300 mg/dl glucose solution used in the concentration dependence test. After 24 hours, the glucose concentration was increased to 397 mg/dl (400 mg/dl) and the oxygen content of the solution was displaced using nitrogen gas. The sensors were then run for a 36-hour period in which pulse testing and EIS were conducted side-by-side every 3 or 6 hours.

By reducing available oxygen and increasing glucose, we endeavored to rapidly decrease the sensitivity of the sensors and transition them into a state in which they would be considered failing sensors ("failed," or "dead"). We created a single criterion for a failed or nonresponsive sensor: calibration factor equal or greater than 50 (cF=[Glu cos e]/Isig).

We assume that failed sensors can have the following properties: 1) low sensitivity to glucose (high CF), and 2) no significant change in impedance magnitude. Given these assumptions, it may be difficult to analyze sensor differences using the pulse test method. Working sensors have a high impedance (can be the same with failed sensors), but are sensitive to changes in glucose concentration. Ideally, a pulse test would be able to identify and differentiate between newly inserted, working (post-init), and failing sensors.

Sensor current response for a failed sensor closely mirrors that of a post-init, working sensor. One interesting property to note is the current response over the first half second: in dead sensors, the peak amplitude is comparable to the amplitude of pre-initialized sensors, whereas in working sensors, the peak amplitude is almost an order of magnitude smaller. The current spike in all of these graphs represents the capacitive element of the impedance—it appears that failing sensors will increase capacitive load while maintaining a similar impedance magnitude. For the data presented, the sensor had been reading with a very high calibration factor after the first few hours of increased glucose and removal of systemic oxygen (cF=397/4.017=98.83, t=10.8 k sec).

The peaks in the step response profile do not line up in time between sensors (different capacitance for each), and existing transmitter hardware has a maximum sampling resolution is 1 Hz. As a result, using current (or differential current) as a diagnostic tool for detecting sensor failure will not be possible, as there is almost no (<1 nA) difference between working and failing sensors. However, the instantaneous pulse can be reflected more clearly in our analysis of charge over time, which will take into account the instantaneous pulse.

The data indicated that using single frequency EIS sampling would be insufficient to differentiate between sensors that are "new," "used," and "dead." EIS sampling at 0.1 Hz performed in sensors with CF>50 showed impedance magnitude and phase measurements that could be mischaracterized as either non-initialized or initialized sensors. An alternative may be to choose specific excitation frequencies for different diagnostic checks −0.1 Hz excitation to differentiate between initialized sensors and non-initialized ones, 100 Hz to differentiate between new sensors and failing ones. Combining this information with other tests (different excitation frequencies) may allow the system to quickly diagnose the state of the sensor.

Example 2

Glucose Sensor Recorder Used in a Canine Model

This example illustrates test methods, data extraction, and analysis involved in testing the current response to small voltage pulse as a method to differentiate between new and used sensors.

DEFINITIONS

| | |
|---|---|
| EIS | Electrochemical Impedance Spectroscopy |
| Count | Analogue to charge; 1 count/sec ~2 nA |
| hex | Hexadecimal (Base-16) |
| HTML | HyperText Markup Language |
| IC | Integrated Circuit |

The complex impedance of a sensor could be used as a diagnostic identifier for sensor life and age (via electrochemical impedance spectroscopy, EIS). Unfortunately, hardware limitations reduce the viability of using an impedance detection IC in existing sensor technology.

One alternative to traditional impedance spectroscopy is to analyze the response of current to a small voltage pulse. By taking into account the peak instantaneous current as well as the total charge over a set amount of time, the sensor transmitter may be able to differentiate between sensors that are inserted and ready, those that are inserted but not completely hydrated, and those that have been inserted and initialized. Depending on sampling frequency and accuracy of measurement, the voltage pulse test can provide a close estimation of the imaginary and real components of impedance across an electrode.

Figure 11:
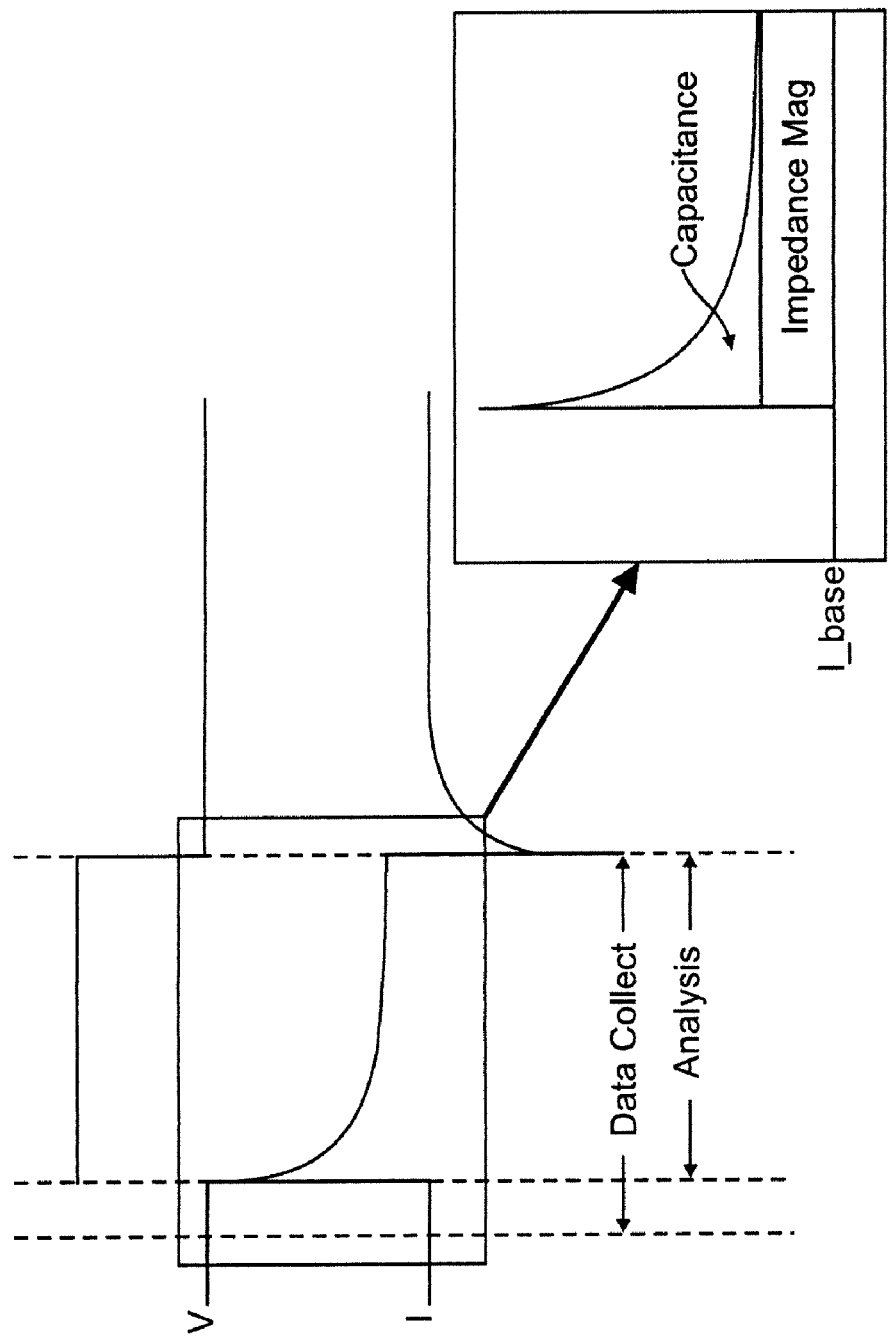
FIG. 11 provides a graph illustrating current response estimation of complex impedance.
Figure 12:
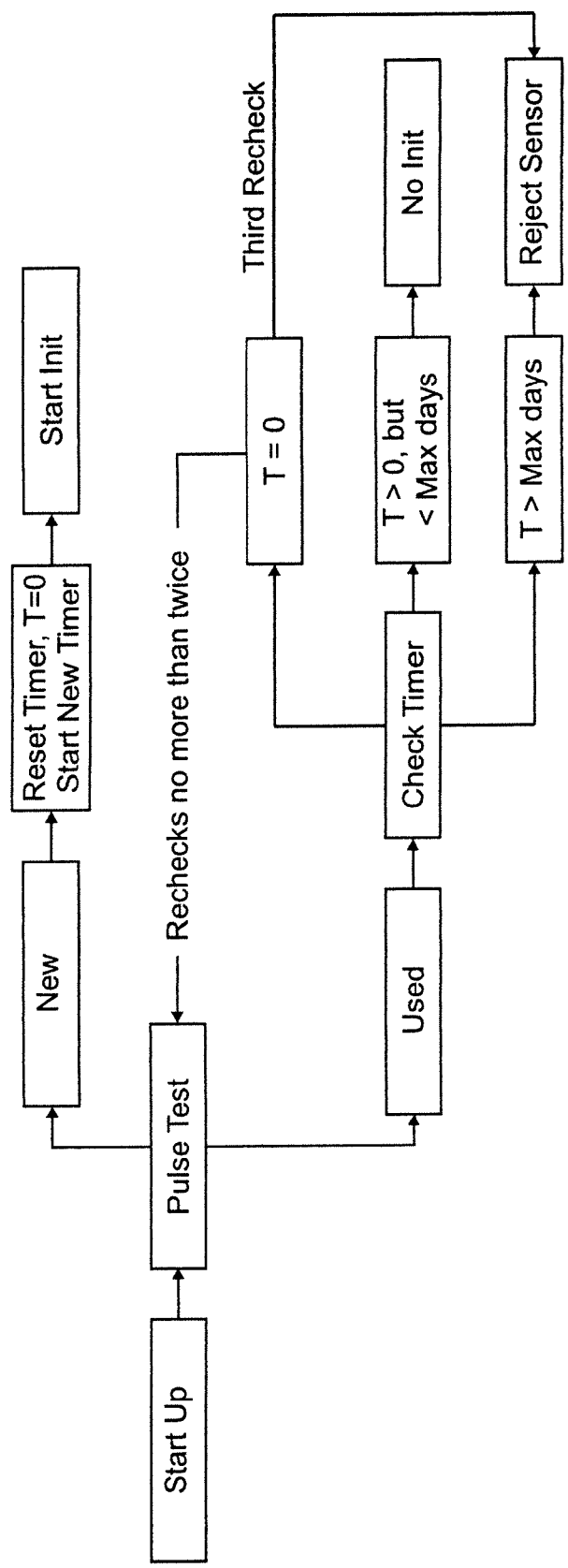
FIG. 12 provides a flow chart illustrating a proposed diagnostic/time limit feedback loop.

Used in conjunction with a software-based timer, this technique can be implemented within existing hardware to set limits on sensor use and help to identify whether sensors can be initialized (prevents re-initialization damage on accidental disconnects). The diagnostic test can also allow for hydration detection, determining not only whether sensors can be initialized but when (see, e.g. FIGS. 11 and 12).

Figure 13:
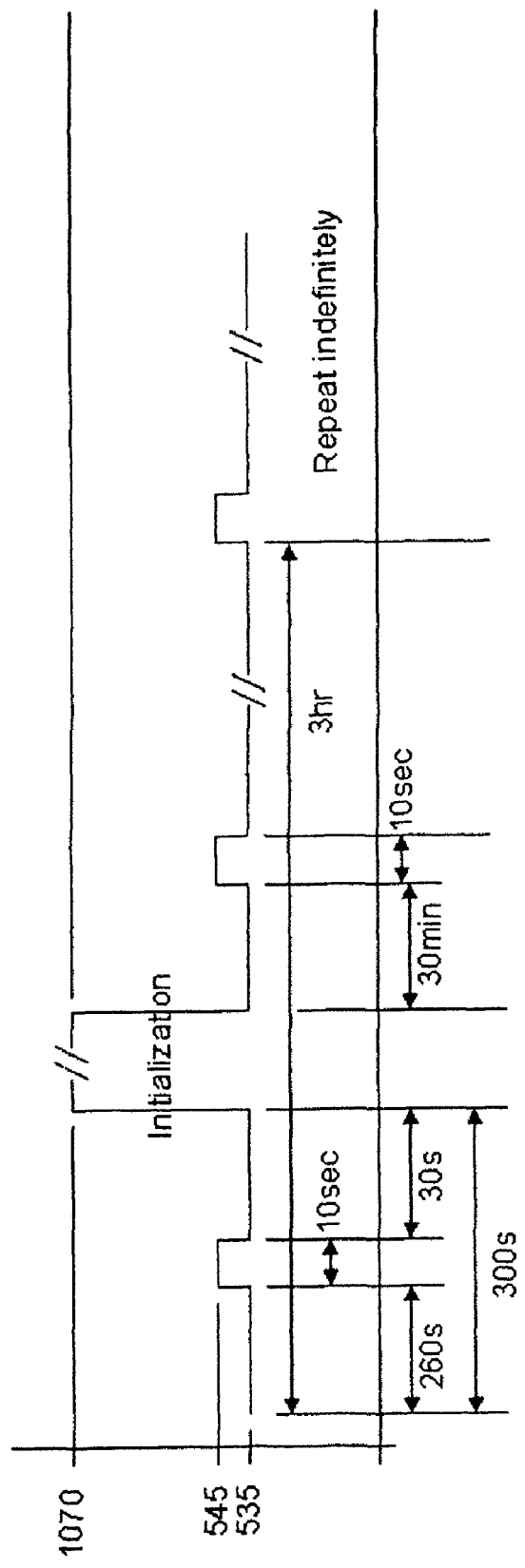
FIG. 13 provides a schematic of customized firmware executing a diagnostic test multiple times.
Figure 14:
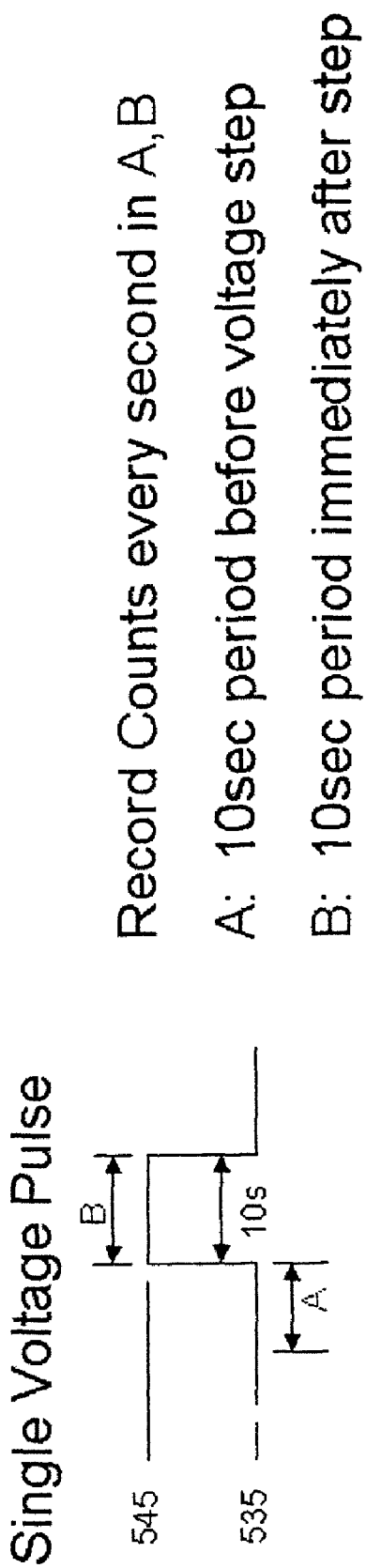
FIG. 14 provides a schematic of data storage for each diagnostic step.

In the trial, sensors with modified firmware were connected for 3 days each to 174 sensors on 18 dogs, spread out over a two-week period. The firmware was modified to add in the pulse-test functionality, and all analysis was conducted post-download using MATLAB. For our purposes, the pulse test was hard-coded to run before initialization, 30 min after initialization, and every three hours following, as shown for example in FIGS. 13 and 14.

The final four studies required that individual recorders be physically disconnected after 48 hours. Sensors were left disconnected between 5 and 10 min before reconnection for a final 24 hours. This change to the protocol was added to observe the accuracy of the pulse test after sensor-disconnect/reconnect cycling.

At the completion of a sensor's 3-day lifetime, the sensor was extracted and the data from the sensor was downloaded in HTML format. The sensor memory was cleared and the unit was placed on the charger in preparation for reuse with a new sensor.

Analysis

In selecting thresholds, the script takes into account the number of true positives and false positives, assigning a 400% relative weight to true positives. The relative scores for combinations of thresholds are tabulated and the highest scores are annotated in the output. The goal of threshold modification is to minimize the amount of false hits (both negative and positive). Strong emphasis is placed on reducing false negatives (a new sensor marked as used is a larger problem than an old sensor marked as new). All analyzed scores are saved to a comma-separated file in a specified directory as threshold_data.csv.

Data and Observations

We were only able to collect html data from 156 of the implanted 174 sensors. Unfortunately, the first 3 studies had GST data which was not downloaded in html format. Of the 156 downloaded files, one was accidentally opened and saved in an alternative format unusable by the existing data parsing script.

At first, the thresholds were set arbitrarily, with the "current amplitude" threshold. Once the dataset was extracted, the threshold analysis script was run on the full dataset. The high and low thresholds with the highest score are listed below (they provided identical results). Deviation from these thresholds would result in either a larger number of false positives or an increase in false negatives.

Figure 15A:
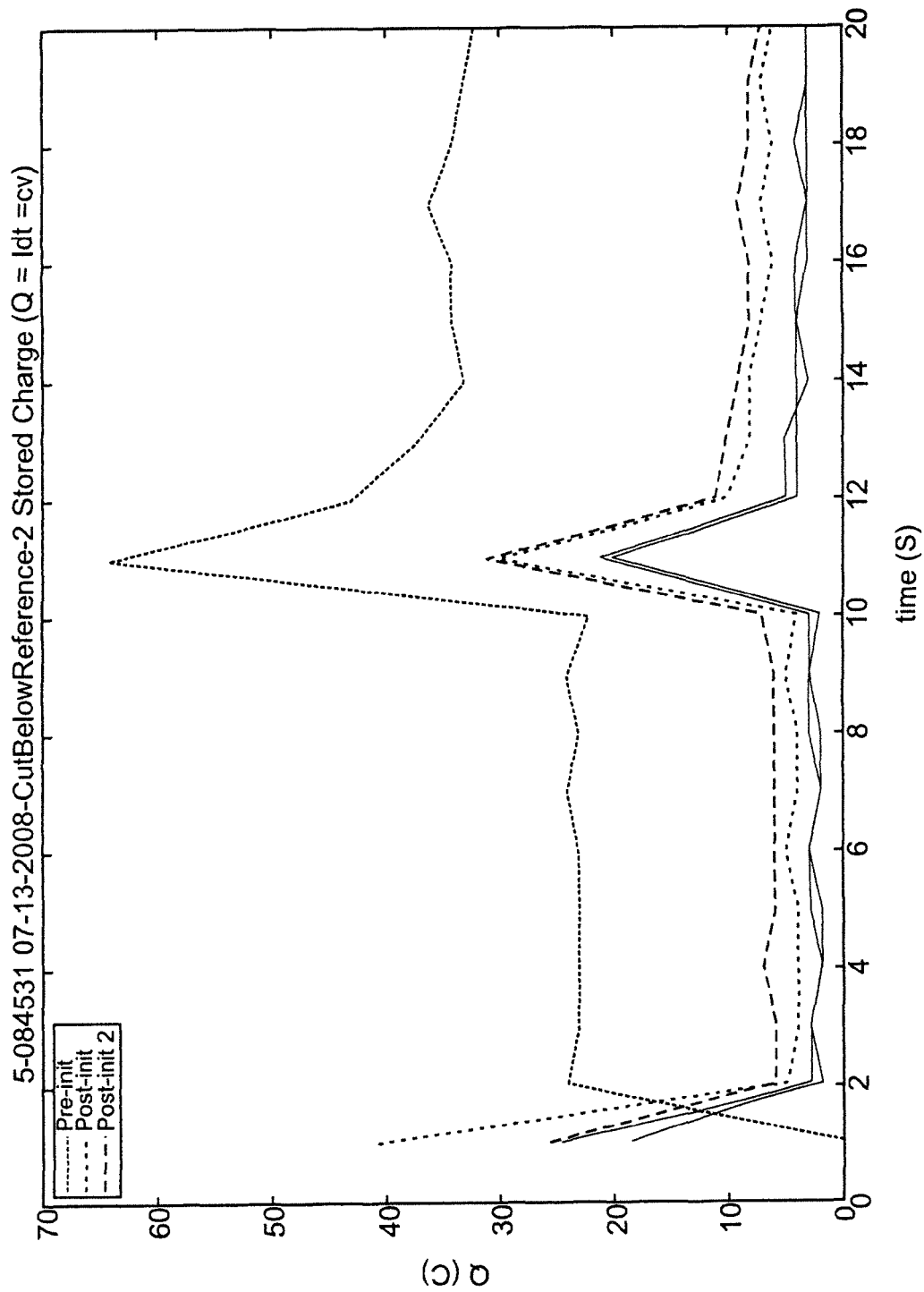
FIGS. 15A and 15B provide graphs illustrating current/capacitance profiles of a hydrated sensor over time.
Figure 15B:
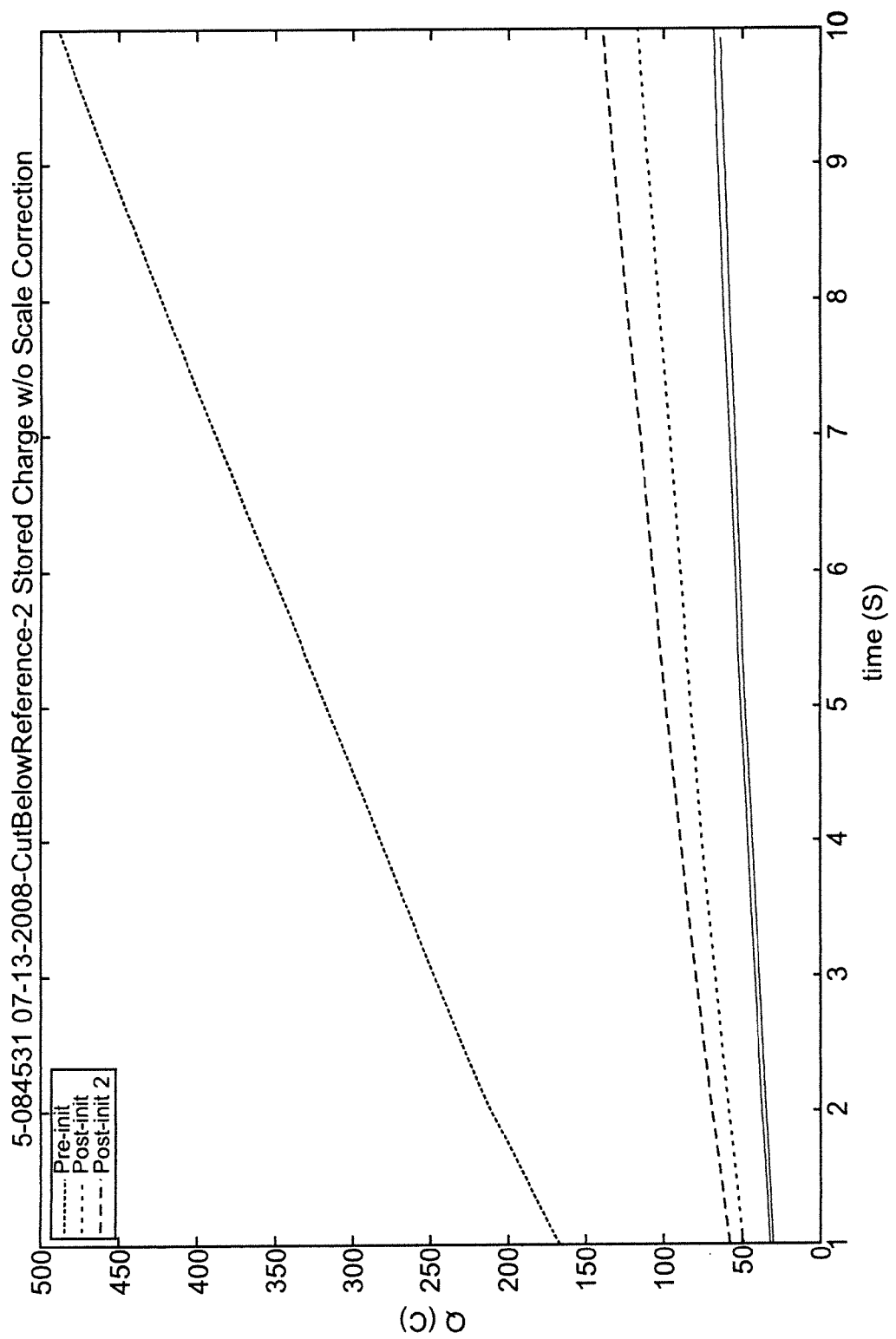

As shown in FIGS. 15A and 15B, we generate two plots for each individual sensor file; each line corresponds to a different pulse test (in time) on the same sensor. The first plot displays the change in counts over the 20 sec-time period in A+B (instantaneous current response). The second plot outputs the differential sum of counts over 10 sec in region B (count amplitude). Note the lack of y-axis scaling control between sensors—use the blue line (second check) as a reference in comparison to the red line (first check) in the following figures.

Figure 16A:
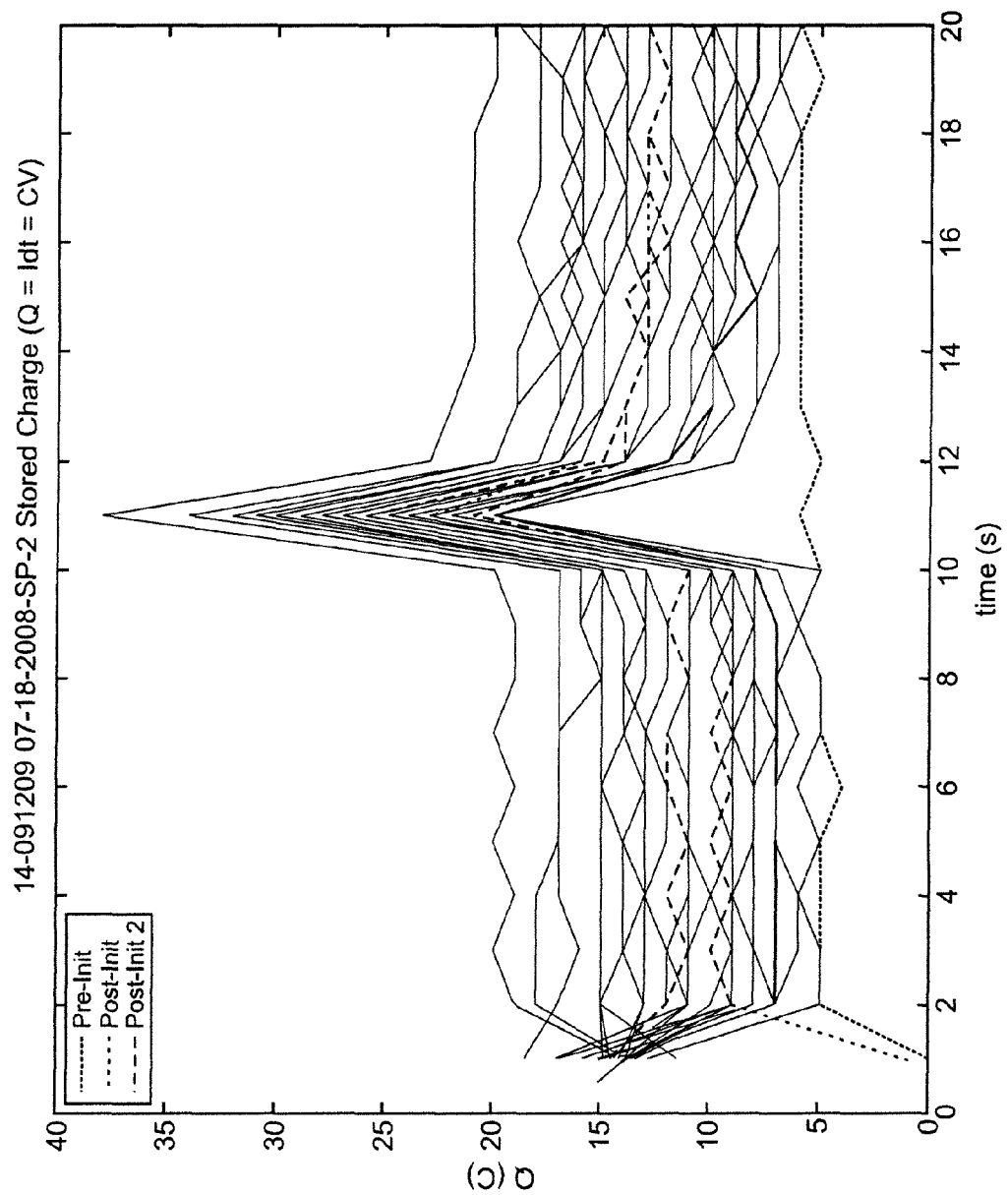
FIGS. 16A and 16B provide graphs illustrating current/capacitance profiles of "sleepy" sensors (e.g. those having hydration issues).
Figure 16B:
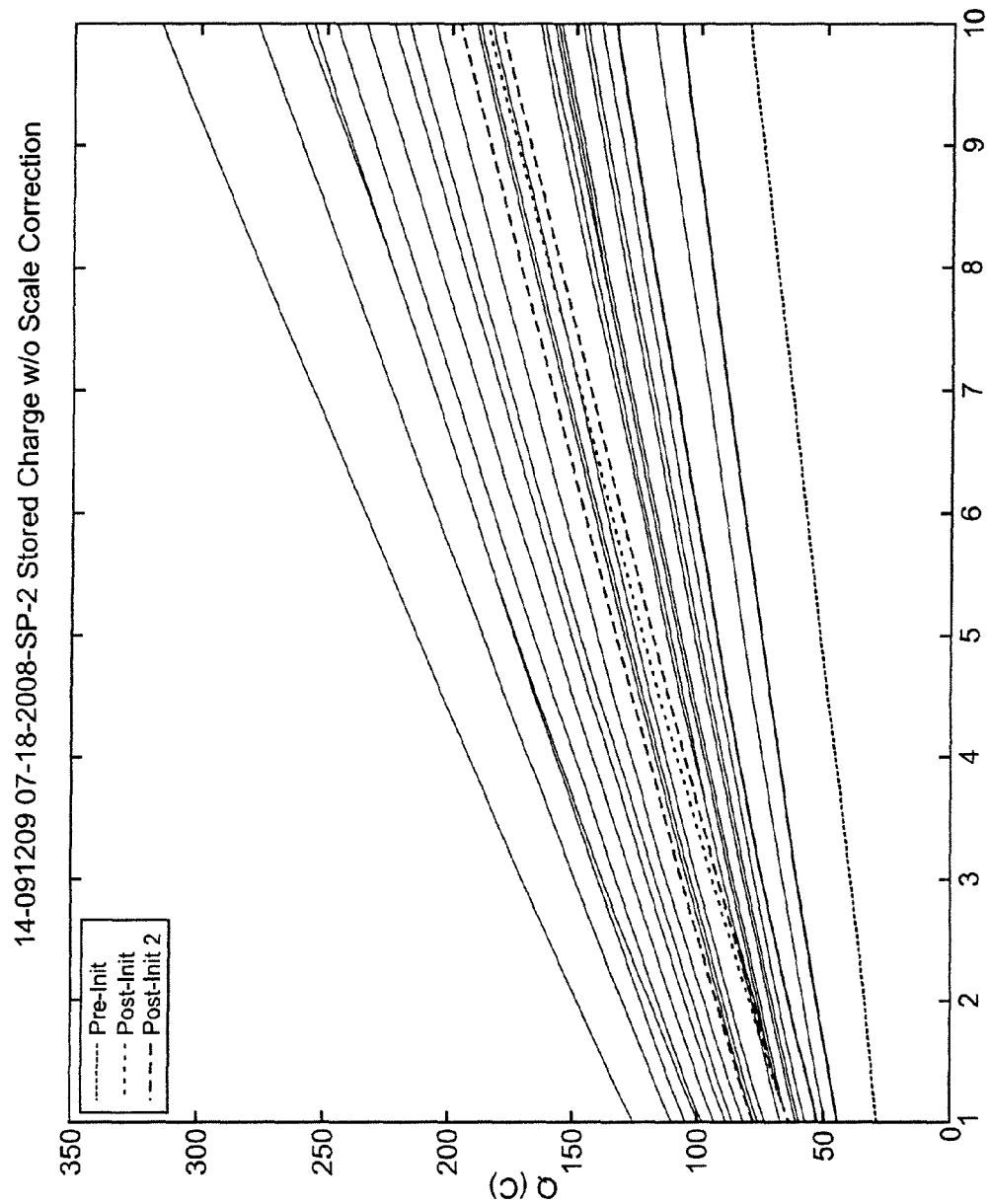

As shown in FIGS. 16A and 16B, newly inserted sensors generate a high instantaneous current (change in counts >30 counts/sec) and a high total charge (>200), as displayed by the red line in each plot. Used sensors show reductions in both current peak and total charge, though the reduction in current peak (change in counts) is less noticeable (blue, black, and grey). With newly inserted sensors that have hydration (or other) issues, the profiles of both graphs will change. In effect, the current response to a voltage stimulus is negligible, and as a result the total charge over time shrinks as well (in a select few cases the current response to the positive voltage step was negative).

Figure 17A:
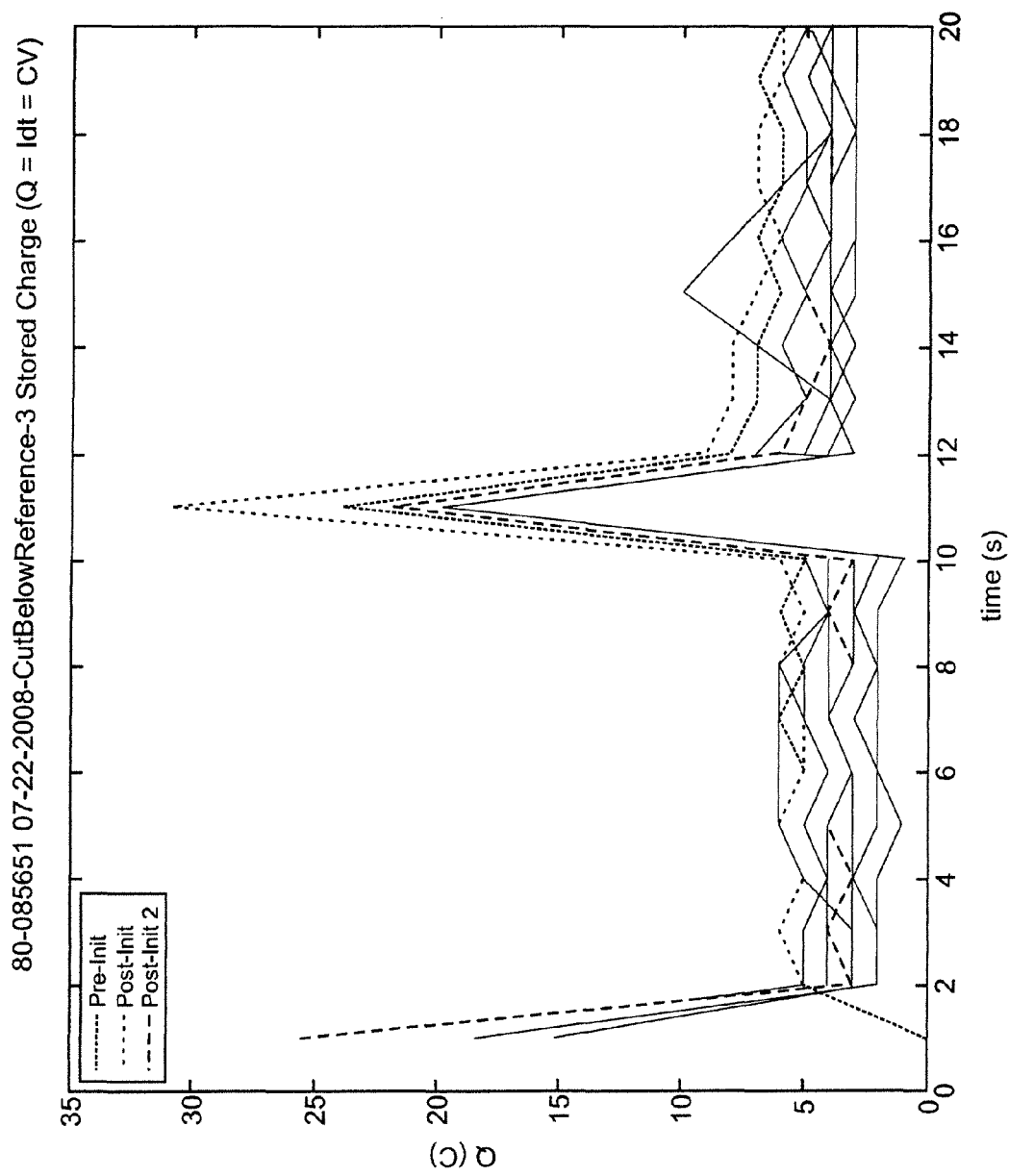
FIGS. 17A and 17B provide graphs illustrating a current/capacitance profile from intentional reinitialization.
Figure 17B:
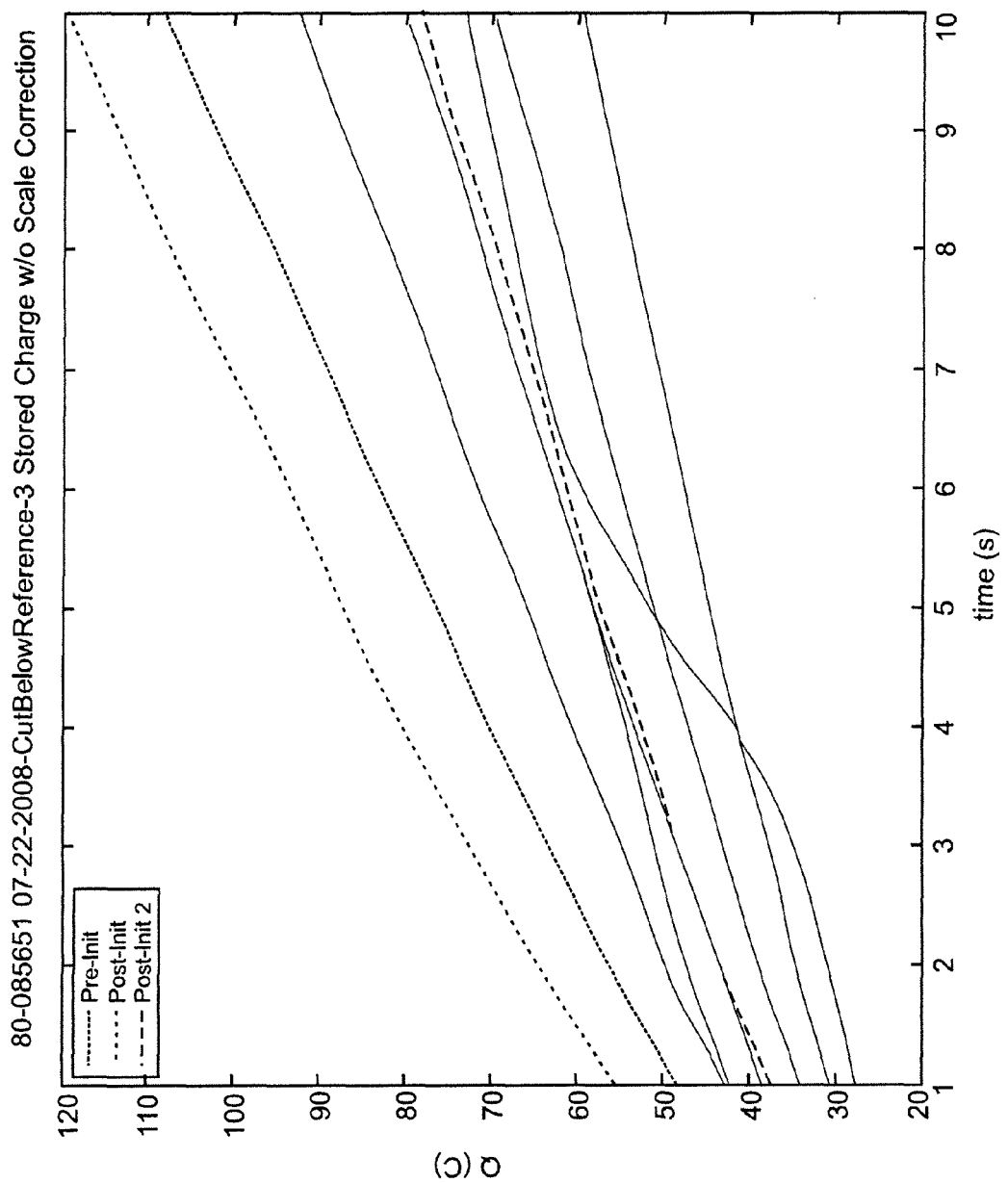
Figure 18:
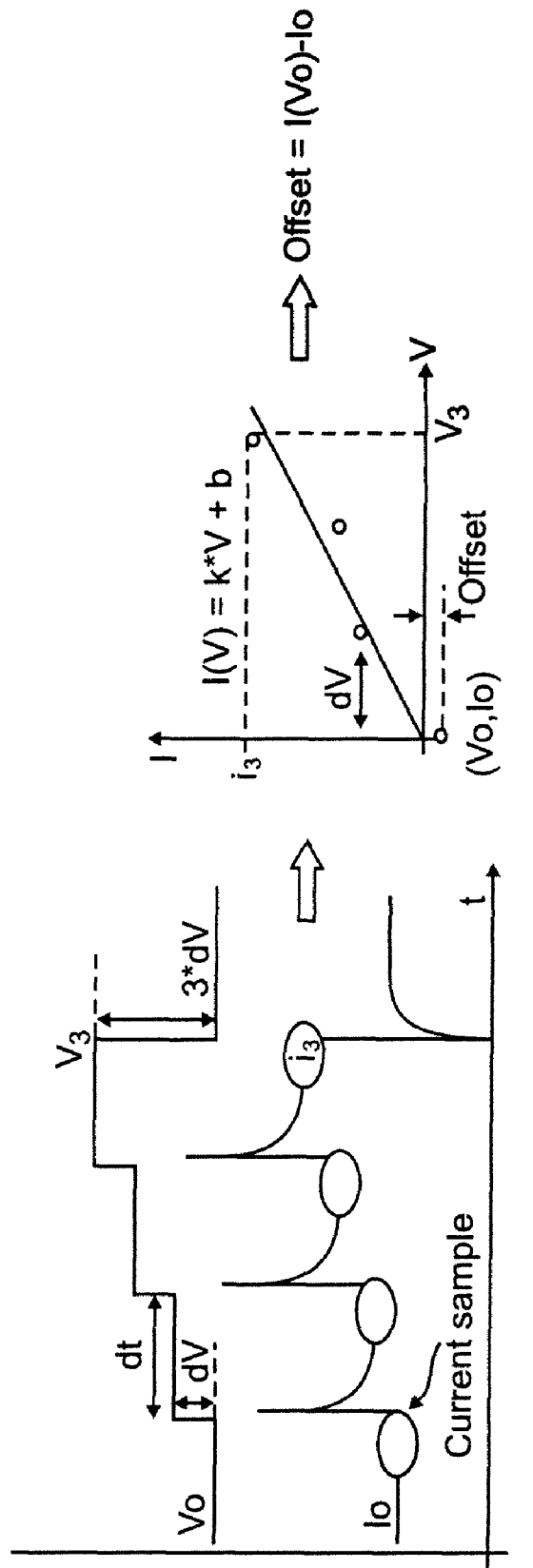
FIG. 18 provides a figurative representation of the theory behind determination of sensor offset. In this figure, V=Potential (Voltage); I=Current (Amp); t=time; I(V)=function for current vs. voltage, using constants k and b based on the linear regression of 4 current-voltage pairs. Vo=stable-state voltage (in our system, 535 mV); Io=stable-state Isig (assume glucose concentration is stable, whatever current is when V=Vo); dV=voltage jump (i.e. 10 mV); dt=time between voltage jumps (i.e. 10 sec); Offset=the current offset inherent in the system. Offset=I($V_o$)−$I_o$. Lowercase v and i are representative of paired times for voltage and corresponding current. A relatively long dt time can be used to confirm current that matches relatively closely with the stable-state current value for that potential. The current is typically not sampled over the entire dt time, (e.g. and instead just the last 1-2 seconds).

As shown in FIGS. 17A and 17B, a group of sensors were intentionally disconnected for 5-10 minutes in the middle of the study. We see that the time in which a sensor is left unpowered does not appear to affect the current response of the sensor (there is no apparent drift from the "used sensor" state back toward that of a newly inserted sensor). The sensor count profile is consistent with plots of old sensors. Furthermore, there does not appear to be any change to sensor response (counts) after a second initialization sequence. The second diagnostic test (blue line) appears post-initialization, and it is theorized that its slightly elevated profiles are a result of post-initialization current overshoot.

Results
  Full Study Statistics
  True Positives: 154 (new sensors marked as new)
  False Positives: 23 (old sensors marked as new)
  True Negatives: 132 (old sensors marked as old)
  False Negatives: 1 (new sensors marked as old)
  For the single false negative: analysis was not able to modify thresholds to mark the sensor as new without causing 95% of old sensors to be incorrectly marked as new.
  New Sensors correctly identified: 99.355%
  Old Sensors correctly identified: 85.161%
  Previously initialized sensors that were reconnected after a short duration generated results as expected, with no false positives from a set of all "negative" data.
  False Positives: 0 (old sensors marked as new)
  True Negatives: 27 (old sensors marked as old)
  The preceding analysis indicates that the differentiation of sensor state is possible. By modifying set thresholds, over 99% of new sensors were correctly identified while 85% of old sensors and 100% of intentional-disconnect sensors were accurately rejected.

Unfortunately, it does not appear as if the system (in current form) has the necessary accuracy and resolution to differentiate between sensors that have become noisy (or lost sensitivity) and those that are running as expected. In previous in vitro analysis (ER08-5327), a bench top potentiostat with millisecond sampling yielded data indicating that there was a measurable difference between capacitance measurements of malfunctioning and working sensors. It is predicted that the move to a newer platform (GST2) will allow for both better resolution and accuracy in measurement.

When moving to clinical trials and human data, thresholds will more than likely need to be revised. With enough human data, the threshold selection script should be able to accurately supply thresholds that will maximize our used-sensor detection (true negative) while minimizing our misidentified new sensors (false positive).

One consideration may be to increase the number of allowed false positives (new sensors recognized as old ones) in order to reduce the number of false negatives (used sensors that are recognized as new ones). The working theory related to false negatives is that they are a direct result of sensor hydration issues. In fact, if the analysis script is modified to ignore Instantaneous Current and only check Total Charge (section 8.2, Individual Lines), resulting failed sensors exhibit a consistent "sleepy" sensor profile (verified by running through the TGMS2 algorithm)—slow run-in time and low sensitivity to glucose concentration for the first 12 hours. If "sleepy sensors" can be eliminated (either by use of revised tubing designs or by the feedback check detailed in FIG. 12), then the number of false negatives should decrease significantly. At the moment, full hydration remains a difficult problem in our analysis of the voltage pulse test.

Use of impedance estimation tests to characterize sensor state has been substantiated. In individual sensors, tests have shown that pulse testing is capable of differentiating between new/working sensors and ones that have lost sensitivity (one failure mode). Further experiments have examined the performance of our voltage pulse test in areas of concern: in varying concentrations of glucose, with non-responsive sensors (dead), and with sensors that are disconnected and reconnected after initialization.

Though there is some variation across individual sensors within the same lot, the general experimental results have been reproduced. Given the data, it appears that thresholds may be determined from which a system will be able to clearly differentiate between newly inserted and initialized sensors. To differentiate between working sensors and those which have lost sensitivity (or high-amplitude noise) will be substantially higher, and should depend on current-sensing resolution.

Thresholds may require modification depending on electrode design, substrate makeup, and process changes. Any change in the sensor design (narrow electrode vs. Distributed electrodes vs. Standard production layout) will result in a change in capacitive response. To reconcile changes in design, the system will need to modify either 1) the thresholds for different sensor states, or 2) the stimulus amplitude to maintain comparable responses.

Future examination should analyze the affect of different electrode layouts on test performance. Other tests would include 1) the specific step amplitude required for adequate resolution, 2) the pulse duration required for test accuracy, 3) examining extended (>12 hour) sensor disconnection, 4) implementation on existing hardware (transmitter hardware, etc).

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

What is claimed is:

1. A method of observing a state of a sensor having a plurality of electrodes, the method comprising:
   (a) applying a voltage to the sensor;
   (b) measuring a stable-state current (Ibase) produced in response to the voltage applied to the sensor;
   (c) applying the stable-state current measured in (b) to the sensor;
   (d) measuring sensor voltage during the application of the stable-state current;
   (e) changing applied sensor current to a second current comprising Ibase+deltaI, wherein deltaI comprises the difference between the Ibase and the second current;
   (f) measuring sensor voltage during the application of the second current;
   (g) observing a first voltage step between the voltage measured in (d) and the voltage measured in (f) that results from electrical resistance (R) in the sensor; so that the state of the sensor is observed;
   (h) changing applied sensor current to a third current comprising Ibase+deltaII, wherein deltaII comprises the difference between the Ibase and the third current;
   (i) measuring sensor voltage during the application of the third current;
   (j) observing a second voltage step between the voltage measured in (d) and/or (f) and/or (i) that results from electrical resistance (R) in the sensor;
   (k) calculating a voltage slope (dV/dt) using multiple voltage step measurements, wherein the voltage slope so calculated is correlated to a change in sensor capacitance (C) that results from the different currents applied to the sensor.

2. The method of claim 1, wherein: calculating resistance (R) in the sensor using a formula R=deltaV/deltaI; and/or calculating capacitance (C) in the sensor using a formula C=deltaI/(dV/dt).

3. The method of claim 1, wherein the sensor is an electrochemical glucose sensor implanted in vivo and the observation of the state of the sensor provides information on:
   sensor hydration;
   sensor noise;
   sensor offset; or
   sensor drift.

4. The method of claim 1, further comprising: performing the method on a plurality of sensors made by differing manufacturing processes.

5. A method of observing a state of a sensor having a plurality of electrodes and a stable-state voltage (Vbase), the method comprising:
   (a) measuring a stable-state current (Ibase) produced in response to the stable-state voltage of the sensor;
   (b) forcing a current using the stable-state current (Ibase) measured in (a);
   (c) changing the forced current to a second current comprising Ibase+deltaI, wherein deltaI comprises the difference between the Ibase and the second current;
   (d) measuring an initially resulting voltage step (deltaV) due to resistance (R) in the sensor;
   (e) changing the forced current to a third current comprising Ibase+deltaII, wherein deltaII comprises the difference between the Ibase and the third current;
   (f) measuring sensor voltage during the application of the third current;
   (g) observing a second voltage step between the voltage measured in (d) and/or (f) that results from electrical resistance (R) in the sensor;
   (h) calculating a voltage slope (dV/dt) using the voltage step measurement in (d), wherein the voltage slope so calculated is related to a charging of a sensor capacitance (C) by the deltaI applied to the sensor;
   (i) calculating resistance (R) in the sensor using a formula R=deltaV/deltaI and calculating capacitance (C) in the sensor using a formula C=deltaI/(dV/dt); so that the state of the sensor is observed.

6. The method of claim 5, wherein the sensor is an electrochemical glucose sensor implanted in vivo and the observation of the state of the sensor provides information on:
   sensor hydration;
   sensor noise;
   sensor offset; or
   sensor drift.

7. The method of claim 5, further comprising: performing the method on a plurality of sensors made by differing manufacturing processes.

8. The method of claim 5, wherein step (b) comprises keeping the sensor at the same voltage while forcing the current to the sensor.

9. The method of claim 5, wherein step (b) comprises allowing the sensor to stabilize at a slightly different voltage while forcing the current to the sensor.

* * * * *